US011633509B2

(12) United States Patent
Ogihara et al.

(10) Patent No.: US 11,633,509 B2
(45) Date of Patent: *Apr. 25, 2023

(54) ULTRAVIOLET RAY IRRADIATION DEVICE AND ULTRAVIOLET RAY BLOCKING UNIT

(71) Applicant: Work Solution Co., Ltd., Nagano (JP)

(72) Inventors: Shinji Ogihara, Nagano (JP); Kiyomi Shimada, Nagano (JP); Haruhiko Miyamoto, Nagano (JP); Eiji Ogihara, Nagano (JP); Kiyohide Nishimura, Nagano (JP); Hirofumi Shimojima, Nagano (JP)

(73) Assignee: WORK SOLUTION CO., LTD., Nagano (JP)

( * ) Notice: Subject to any disclaimer, the term of this patent is extended or adjusted under 35 U.S.C. 154(b) by 232 days.

This patent is subject to a terminal disclaimer.

(21) Appl. No.: 17/105,652

(22) Filed: Nov. 27, 2020

(65) Prior Publication Data

US 2021/0177999 A1 Jun. 17, 2021

(30) Foreign Application Priority Data

Dec. 12, 2019 (JP) ................ JP2019-224753

(51) Int. Cl.
*A61L 2/10* (2006.01)
*B08B 7/00* (2006.01)
*G01J 5/00* (2022.01)
*A61L 2/26* (2006.01)

(52) U.S. Cl.
CPC ...................... *A61L 2/10* (2013.01); *A61L 2/26* (2013.01); *B08B 7/0057* (2013.01); *G01J 5/0025* (2013.01); *A61L 2202/11* (2013.01); *A61L 2202/14* (2013.01)

(58) Field of Classification Search
CPC .......... A61L 2/10; A61L 2/26; A61L 2202/11; A61L 2202/14; B08B 7/0057; G01J 5/0025
USPC .............................. 250/453.11, 454.11, 455.11
See application file for complete search history.

(56) References Cited

U.S. PATENT DOCUMENTS

2021/0353807 A1* 11/2021 Ogihara .................. A61L 2/10

FOREIGN PATENT DOCUMENTS

JP 201763900 A 4/2017

* cited by examiner

*Primary Examiner* — Nicole M Ippolito
(74) *Attorney, Agent, or Firm* — Hauptman Ham, LLP

(57) ABSTRACT

To provide an ultraviolet ray irradiation device by preventing leakage of ultraviolet rays from an insertion opening through which a hand on which a glove is mounted is inserted into a sterilization chamber. The device includes: an ultraviolet ray blocking balloon disposed in an insertion opening; a pressurized gas supplying and discharging device which supplies a gas under pressure to the balloon and discharges from it; an insertion depth detection unit which outputs an insertion hand depth detection signal; a controller of an ultraviolet ray irradiation and a pressurized gas supplying and discharging, wherein the balloon forms an opening which allows an insertion and a removal of the hand before the gas is supplied, and it is inflated with the supply of the gas so as to be brought into close contact with a wrist portion of the glove, and it is deflated with a discharge of the gas.

12 Claims, 10 Drawing Sheets

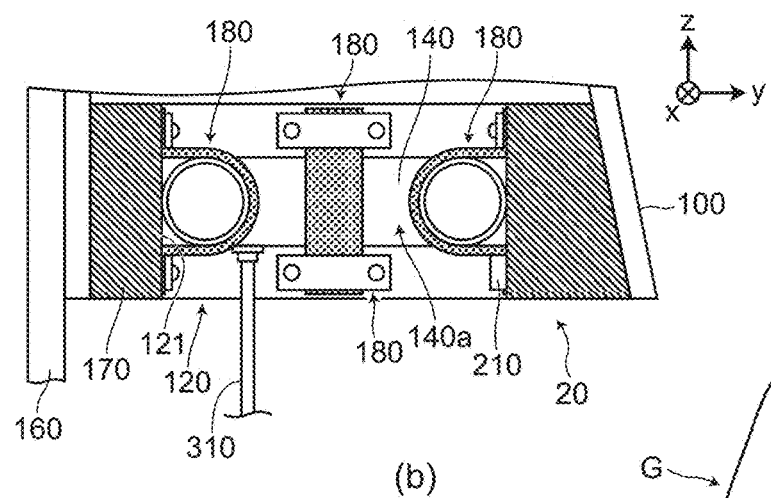
FIG.7A
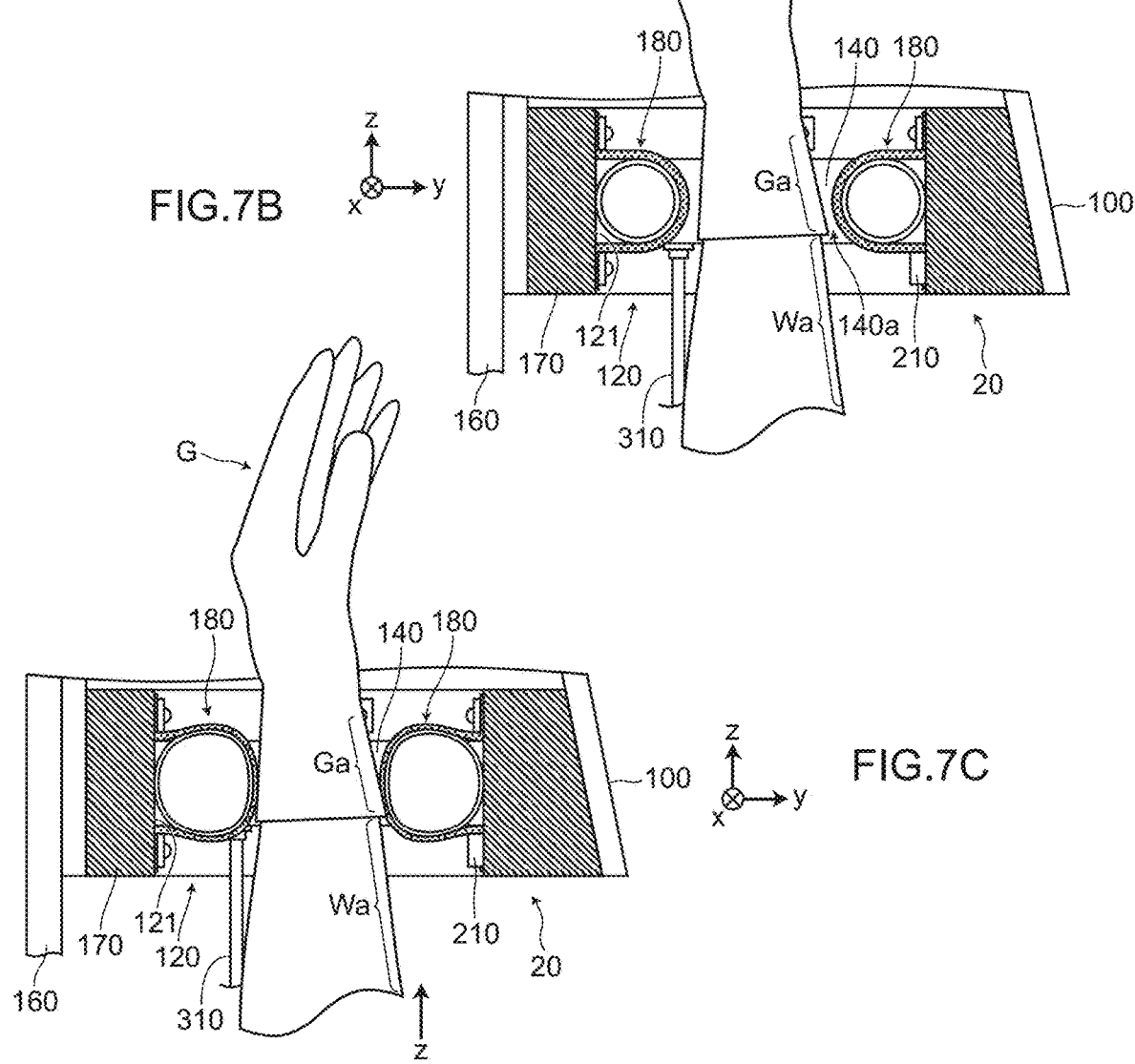
FIG.7B
FIG.7C

ULTRAVIOLET RAY IRRADIATION DEVICE AND ULTRAVIOLET RAY BLOCKING UNIT

RELATED APPLICATIONS

The present application claims priority to Japanese Application Number 2019-224753, filed Dec. 12, 2019, the disclosure of which is hereby incorporated by reference herein in its entirety.

BACKGROUND OF THE INVENTION

Field of the Invention

The present invention relates to an ultraviolet ray irradiation device and an ultraviolet ray blocking unit.

Description of the Related Art

Sterilization by ultraviolet rays exhibits a highly favorable effect against bacteria in a wide range including norovirus, salmonella and O157. Accordingly, in various fields including food industry and medical field, an ultraviolet ray irradiation device which uses ultraviolet rays has been attracting attentions.

Although ultraviolet rays exhibit a highly favorable effect against bacteria in a wide range, on the other hand, there has been also reported that, when ultraviolet rays are irradiated to an operator or other operators around him, the ultraviolet rays adversely affect the operator or other operators around him. Accordingly, it is important for an ultraviolet ray irradiation device to ensure high safety such that ultraviolet rays irradiated in a sterilization chamber defined in a sterilization chamber housing do not adversely affect an operator or other operators around him. Therefore, an ultraviolet ray irradiation device which exhibits high safety has been proposed by taking into account the above problem (see JP 2017-63900 A, for example).

FIG. 13 is a perspective view for describing an ultraviolet ray irradiation device 900 described in JP 2017-63900 A. The ultraviolet ray irradiation device 900 described in JP 2017-63900 A includes, as shown in FIG. 13, a sterilization chamber housing 920 having an insertion opening 910 through which a hand on which a glove G is mounted is inserted; ultraviolet ray irradiation lamps 930 which irradiate ultraviolet rays to a sterilization chamber 921 formed in the sterilization chamber housing 920; a guide portion 940 having a sleeve shape extending from an edge portion of the insertion opening 910 in a direction toward an inside of the sterilization chamber 921, guiding an insertion of the hand on which the glove is mounted and blocking the ultraviolet rays; and an ultraviolet ray blocking plate 950 which covers a front surface and side surfaces of the insertion opening 910.

The ultraviolet ray irradiation device 900 described in JP 2017-63900 A is an ultraviolet ray irradiation device of a type where the hand on which the glove G is mounted is inserted in a downward direction from above. On the other hand, with respect to the ultraviolet ray irradiation device 900, an ultraviolet ray irradiation device of a type where the hand on which the glove G is mounted is inserted in an upward direction from below is also described.

The ultraviolet ray irradiation device 900 described in JP 2017-63900 A is an ultraviolet ray irradiation device which sterilizes a surface of the glove G by irradiating ultraviolet rays to the glove G which is mounted on a hand of an operator. In other words, when the hand of the operator on which the glove G is mounted is inserted into the sterilization chamber 921 through the insertion opening 910, the ultraviolet ray irradiation lamps 930 are turned on in the sterilization chamber 921 so that ultraviolet rays are irradiated to the surface of the glove G. With such a configuration, the surface of the glove G can be sterilized.

Further, the ultraviolet ray irradiation device 900 described in JP 2017-63900 A includes, as described above, the guide portion 940 having a sleeve shape and the ultraviolet ray blocking plate 950. Accordingly, it is possible to prevent the occurrence of a state where ultraviolet rays which are irradiated to the sterilization chamber 921 are irradiated to an operator who is receiving sterilization at the moment and other operators around the operator. As a result, the ultraviolet ray irradiation device 900 described in JP 2017-63900 A may be an ultraviolet ray irradiation device having high safety which does not adversely affect the operator who is receiving sterilization at the moment and other operators around the operator.

SUMMARY OF THE INVENTION

As described above, the ultraviolet ray irradiation device 900 described in JP 2017-63900 A is an ultraviolet ray irradiation device which exhibits high safety. However, there has been a demand the development of an ultraviolet ray irradiation device having higher safety. Under such a circumstance, if ultraviolet rays leaked out from an insertion opening can be blocked with certainty, it is possible to prevent the occurrence of a state where ultraviolet rays are irradiated to an operator who is receiving sterilization at the moment and other operators around the operator. Accordingly, to realize an ultraviolet ray irradiation device which further enhances safety, it is necessary to prevent ultraviolet rays from being irradiated to the outside of a sterilization chamber with certainty when an operator inserts a glove into the ultraviolet ray irradiation device.

Particularly, depending on the content of an operation which an operator performs, there arises a case where the operator uses a short glove which cannot cover a portion ranging from a wrist to an elbow of the operator, and the operator also cannot wear an arm cover which covers the wrist and the elbow portion. In such a case, a hand on which a glove G is mounted is inserted into the sterilization chamber 921 through the insertion opening 910 in a state where the wrist and the elbow of the operator are exposed, that is, in a state where the wrist and the elbow are in a bare skin state. In this case, the wrist and the elbow of the operator are positioned outside of the insertion opening. However, when ultraviolet rays are leaked to the outside from the ultraviolet ray irradiation device, there arises a possibility that the leaked ultraviolet rays are irradiated also to the wrist and the elbow. To cope with also such a case, it is important to prevent with certainty the irradiation of ultraviolet rays to the outside of the ultraviolet ray irradiation device.

The present invention has been made in view of the above-mentioned circumstances, and it is an object of the present invention to provide an ultraviolet ray irradiation device which sterilizes a surface of a glove which is mounted on a hand of an operator and is made of an ultraviolet ray non-transmitting material by irradiating ultraviolet rays to the glove, wherein the ultraviolet ray irradiation device can further enhance safety by preventing with certainty the irradiation of the ultraviolet rays to the outside of the ultraviolet ray irradiation device when the glove of the operator is inserted into the ultraviolet ray irradiation device.

It is another object of the present invention to provide art ultraviolet ray blocking unit which can prevent with certainty the irradiation of ultraviolet rays to the outside of the ultraviolet ray irradiation device when a glove of an operator is inserted into the ultraviolet ray irradiation device and can facilitate a maintenance of the ultraviolet ray irradiation device.

[1] According to an aspect of the present invention, there is provided an ultraviolet ray irradiation device which sterilizes a surface of a glove which is mounted on a hand of an operator and is made of an ultraviolet ray non-transmitting material by irradiating ultraviolet rays to the glove, the ultraviolet ray irradiation device includes: a sterilization chamber housing formed of an ultraviolet ray blocking member configured to block the ultraviolet rays, the sterilization chamber housing having a sterilization chamber in the sterilization chamber housing, and having an insertion opening through which the hand on which the glove is mounted is insertable into the sterilization chamber; an ultraviolet ray irradiation unit disposed in the sterilization chamber housing and configured to irradiate the ultraviolet rays to the sterilization chamber; an ultraviolet ray blocking balloon having a sleeve shape, the ultraviolet ray blocking balloon being disposed along an edge portion of the insertion opening, the ultraviolet ray blocking balloon being made of an ultraviolet ray non-transmitting material; a pressurized gas supplying and discharging device configured to supply a gas under pressure to the ultraviolet ray blocking balloon and to discharge the gas supplied under pressure; an insertion depth detection unit configured to output an insertion depth detection signal when the hand on which the glove is mounted is brought into a state where the hand is inserted into the sterilization chamber by a predetermined depth is detected; and a controller configured to perform an ultraviolet ray irradiation control of the ultraviolet ray irradiation unit and a pressurized gas supplying and discharging control of the pressurized gas supplying and discharging device based on the insertion depth detection signal outputted from the insertion depth detection unit, wherein the ultraviolet ray blocking balloon forms an opening which allows an insertion and a removal of the hand on which the glove is mounted before the gas is supplied under pressure to the ultraviolet ray blocking balloon, the ultraviolet ray blocking balloon is inflated with a supply of the gas under pressure to the ultraviolet ray blocking balloon and surrounds a wrist portion of the glove in a state where the ultraviolet ray blocking balloon is brought into close contact with the wrist portion of the glove, and the ultraviolet ray blocking balloon is deflated with a discharge of the gas supplied under pressure and forms the opening which allows the insertion and the removal of the hand on which the glove is mounted.

[2] In the ultraviolet ray irradiation device according to the present invention, it is preferable that the insertion depth detection unit be a bare skin detection unit configured to detect a bare skin of the operator, the bare skin detection unit be disposed at a position where a bare skin region right below the wrist portion of the glove can be detected when the hand on which the glove is mounted is brought into a state where the hand is inserted into the sterilization chamber by a predetermined depth, and be configured to output a base skin detection signal as the insertion depth detection signal when the bare skin region is detected.

[3] in the ultraviolet ray irradiation device according to the present invention, it is preferable that the insertion depth detection unit be an operator identifier detection unit configured to detect an operator identifier attached to the wrist portion of the glove, the operator identifier detection unit be disposed at a position where the operator identifier can be detected when the hand on which the glove is mounted is brought into a state where the hand is inserted into the sterilization chamber by the predetermined depth, and be configured to output an operator identifier detection signal as the insertion depth detection signal when the operator identifier is detected.

[4] in the ultraviolet ray irradiation device according to the present invention, it is preferable that the pressurized gas supplying and discharging device include: a compressed gas generating unit for generating a compressed gas; a gas flow pipe disposed between the compressed gas generating unit and the ultraviolet ray blocking balloon and forming a flow path for the gas; a flow path switching valve disposed on an intermediate portion of the gas flow pipe; and a flow rate regulating valve mounted on the gas flow pipe disposed between the flow path switching valve and the ultraviolet ray blocking balloon, wherein the flow path switching valve have a function of switching a flow direction of a gas which flows through the gas flow pipe between a flow direction on a pressurized gas supply side where the gas is supplied under pressure to the ultraviolet ray blocking balloon and a flow direction on a pressurized gas discharge side where the gas supplied under pressure to the ultraviolet ray blocking balloon is discharged to an outside, and the flow rate regulating valve have a function of switching a flow rate of a gas which flows through the gas flow pipe between a flow rate on the pressurized gas supply side where the gas is supplied under pressure to the ultraviolet ray blocking balloon and a flow rate on the pressurized gas discharge side where the gas supplied under pressure to the ultraviolet ray blocking balloon is discharged to the outside, the flow rate on the pressurized gas supply side being set smaller than the flow rate on the pressurized gas discharge side.

[5] In the ultraviolet ray irradiation device according to the present invention, it is preferable that the pressurized gas supplying and discharging device further include a pressure regulating valve which has a function of regulating a pressure of a gas which the compressed gas generating unit generates to a predetermined pressure.

[6] In the ultraviolet ray irradiation device according to the present invention, it is preferable that the controller be configured to perform a control of switching a flow direction of the gas to the flow direction on the pressurized gas supply side with respect to the flow path switching valve based on the insertion depth detection signal outputted from the insertion depth detection unit, to perform a control of switching a flow rate of the gas to the flow rate on the pressurized gas supply side with respect to the flow rate regulating valve, to perform a control of generating the gas with respect to the compressed gas generating unit, thereafter, to perform a control of starting irradiation of ultraviolet rays with respect to the ultraviolet ray irradiation unit, and when the ultraviolet ray irradiation unit performs the irradiation of the ultraviolet rays for a predetermined time, the controller be configured to perform a control of finishing the irradiation of the ultraviolet rays with respect to the ultraviolet ray irradiation unit, thereafter, to perform a control of stopping generation of a compressed gas with respect to the compressed gas generating unit, to perform a control of switching the flow direction of the gas to the flow direction on the pressurized gas discharge side with respect to the flow path switching valve, and to perform a control of switching a flow rate of the gas to the flow rate on the pressurized gas discharge side with respect to the flow rate regulating valve.

[7] In the ultraviolet ray irradiation device according to the present invention, it is preferable that a plurality of deflation assist belts each having stretching and shrinking property for assisting deflation of the ultraviolet ray blocking balloon be mounted on a plurality of portions of an edge portion of the insertion opening in a circumferential direction in a spaced-apart manner from each other, and each of the deflation assist belt have a U-shaped folded shape, support a peripheral surface of the ultraviolet ray blocking balloon on an inner surface side of a folded portion of the deflation assist belt having the U-shaped folded shape, and both end portions of the deflation assist belt having the U-shaped folded shape be mounted on the edge portion of the insertion opening.

[8] In the ultraviolet ray irradiation device according to the present invention, it is preferable that the ultraviolet ray blocking balloon have an annular shape, and the ultraviolet ray blocking balloon having the annular shape be disposed so as to surround the edge portion of the insertion opening one turn along the edge portion.

[9] In the ultraviolet ray irradiation device according to the present invention, it is preferable that the ultraviolet ray blocking balloon be formed of a plurality of ultraviolet ray blocking balloons, the plurality of ultraviolet ray blocking balloons be arranged in a longitudinal row so as to surround the edge portion of the insertion opening one turn along the edge portion.

[10] In the ultraviolet ray irradiation device according to the present invention, it is preferable that a groove having a concave shape be formed on an edge portion of an insertion opening so as to extend along the edge portion one turn in a circumferential direction, and a surface of the ultraviolet ray blocking balloon on a side along the edge portion of the insertion opening be accommodated in the groove having a concave shape.

[11] In the ultraviolet ray irradiation device according to the present invention, it is preferable that antibacterial treatment be applied to a surface of the ultraviolet ray blocking balloon.

[12] According to another aspect of the present invention, there is provided an ultraviolet ray blocking unit which is mounted on an ultraviolet ray irradiation device which sterilizes a surface of a glove which is mounted on a hand of an operator and is made of an ultraviolet ray non-transmitting material by irradiating ultraviolet rays to the glove, the ultraviolet ray blocking unit configured to prevent an irradiation of the ultraviolet rays to an outside of the ultraviolet ray irradiation device when the glove of the operator inserted into the ultraviolet ray irradiation device, wherein the ultraviolet ray irradiation device includes: a sterilization chamber housing formed of art ultraviolet ray blocking member configured to block the ultraviolet rays, the sterilization chamber housing having a sterilization chamber in the sterilization chamber housing, and having an insertion opening through which the hand on which the glove is mounted is insertable into the sterilization chamber; an ultraviolet ray irradiation unit disposed in the sterilization chamber housing and configured to irradiate the ultraviolet rays to the sterilization chamber; an ultraviolet ray blocking balloon having a sleeve shape, the ultraviolet ray blocking balloon being disposed along an edge portion of the insertion opening, the ultraviolet ray blocking balloon being made of an ultraviolet ray non-transmitting material; a pressurized gas supplying and discharging device configured to supply a gas under pressure to the ultraviolet ray blocking balloon and to discharge the gas supplied under pressure; an insertion depth detection unit configured to output an insertion depth detection signal when the hand on which the glove is mounted is brought into a state where the hand is inserted into the sterilization chamber by a predetermined depth is detected; and a controller configured to perform an ultraviolet ray irradiation control of the ultraviolet ray irradiation unit and a pressurized gas supplying and discharging control of the pressurized gas supplying and discharging device based on the insertion depth detection signal outputted from the insertion depth detection unit, wherein the ultraviolet ray blocking balloon forms an opening which allows an insertion and a removal of the hand on which the glove is mounted before the gas is supplied under pressure to the ultraviolet ray blocking balloon, the ultraviolet ray blocking balloon is inflated with a supply of the gas under pressure to the ultraviolet ray blocking balloon and surrounds a wrist portion of the glove in a state where the ultraviolet ray blocking balloon is brought into close contact with the wrist portion of the glove, and the ultraviolet ray blocking balloon is deflated with a discharge of the gas supplied under pressure and forms the opening which allows the insertion and the removal of the hand on which the glove is mounted, and the sterilization chamber housing includes a sterilization chamber housing member in which the insertion opening is formed, and which forms one surface of the sterilization chamber housing by being mounted on the sterilization chamber housing, and the ultraviolet ray blocking unit includes: the sterilization chamber housing member; and the ultraviolet ray blocking balloon disposed along the edge portion of the insertion opening formed in the sterilization chamber housing member, and is detachably mounted on the sterilization chamber housing.

According to the ultraviolet ray irradiation device of the present invention, in the ultraviolet ray irradiation device which sterilizes a surface of a glove which is mounted on a hand of an operator and is made of an ultraviolet ray non-transmitting material by irradiating ultraviolet rays to the glove, the ultraviolet ray irradiation device can further enhance safety by preventing with certainty the irradiation of the ultraviolet rays to the outside of the ultraviolet ray irradiation device when the glove of the operator is inserted into the ultraviolet ray irradiation device.

Further, according to the ultraviolet ray blocking unit of the present invention, the ultraviolet ray blocking unit can prevent with certainty the irradiation of ultraviolet rays to the outside of an ultraviolet ray irradiation device when a glove of an operator is inserted into the ultraviolet ray irradiation device and can facilitate a maintenance of the ultraviolet ray irradiation device.

BRIEF DESCRIPTION OF THE DRAWINGS

FIG. 7A to FIG. 7C are views for describing an operation of an ultraviolet ray blocking balloon 140;

FIG. 8 is a plan view showing an appearance in which the ultraviolet ray blocking balloon 140 surrounds a wrist portion Ga of a glove G in a state where the ultraviolet ray blocking balloon 140 is brought into close contact with the wrist portion Ga of the glove G as viewed in the direction indicated by the arrow a;

DETAILED DESCRIPTION OF THE PREFERRED EMBODIMENTS

Figure 1:
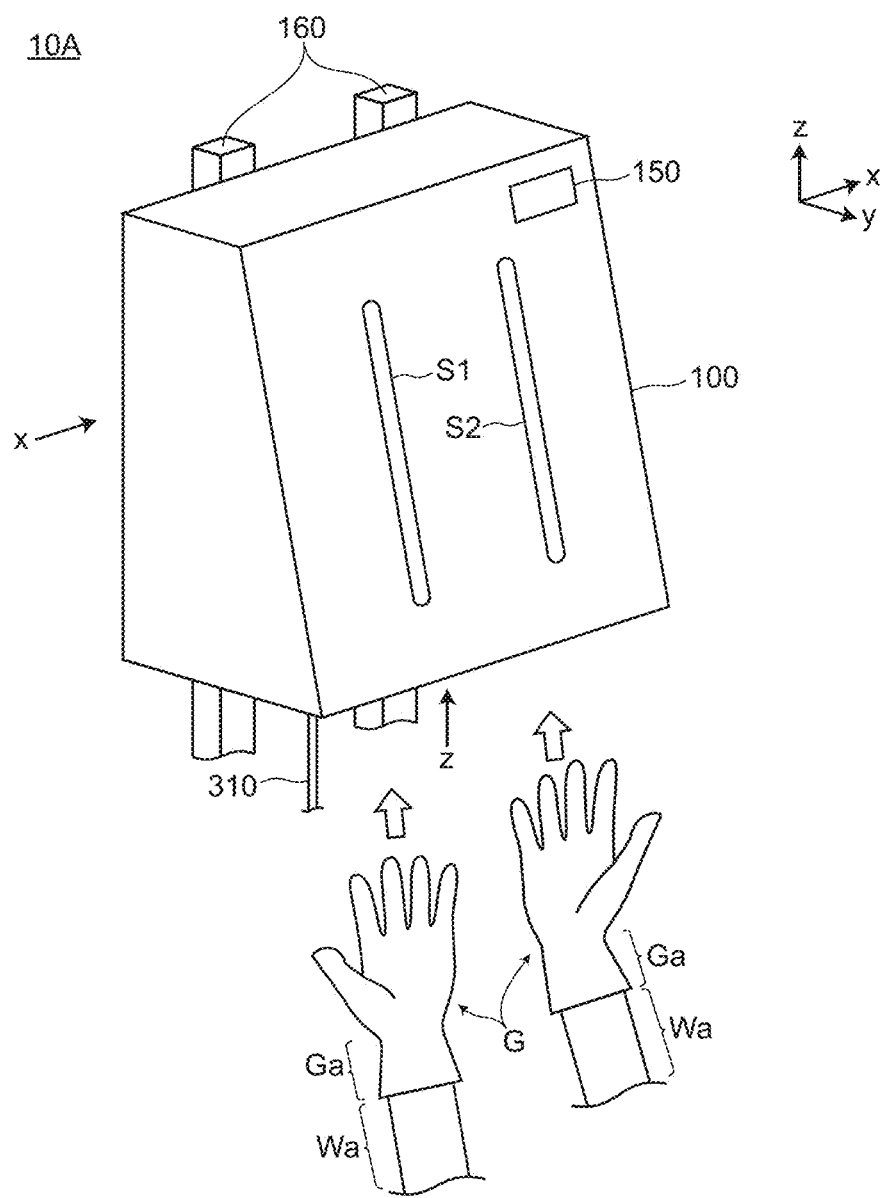
FIG. 1 is a perspective view of an external appearance of an ultraviolet ray irradiation device 10A according to an embodiment 1.

Hereinafter, an ultraviolet ray irradiation device according to the present invention and an ultraviolet ray blocking unit according to the present invention are described based on respective embodiments described below. The structures and the like shown in respective drawings which describe the respective embodiments are schematic views and hence, the indication of sizes and angles does not always reflect actual sizes and angles.

Embodiment 1

First, the configuration of an ultraviolet ray irradiation device 10A according to an embodiment 1 is described with reference to FIG. 1 to FIG. 4. As shown in FIG. 1 to FIG. 4, the ultraviolet ray irradiation device 10A according to the embodiment 1 includes: a sterilization chamber housing 100 which has a sterilization chamber 110 therein and insertion openings 120 through each of which a hand on which glove G is mounted is inserted into the sterilization chamber 110; an ultraviolet ray irradiation unit 130 which is disposed in the sterilization chamber housing 100 and irradiates ultraviolet rays to the sterilization chamber 110; ultraviolet ray blocking balloons 140 each having a cylindrical shape disposed along an edge portion 121 of the insertion opening 120 and is made of an ultraviolet ray non-transmitting material; a display unit 150 disposed on a front surface of the sterilization chamber housing 100; and support struts 160 which elevatably support the sterilization chamber housing 100 along a z axis. The ultraviolet ray irradiation unit 130 is formed of a plurality of ultraviolet ray irradiation lamps. Accordingly, in the description made hereinafter, there is also a case where "ultraviolet ray irradiation unit 130" are expressed as "a plurality of ultraviolet ray irradiation lamps 130" or simply expressed as "ultraviolet ray irradiation lamp 130". The ultraviolet ray blocking balloon 140 is described in detail later.

The ultraviolet ray irradiation device 10A according to the embodiment 1 includes bare skin detection units 210 each of which forms an insertion depth detection unit which detects that the hand on which the glove G is mounted is inserted into the sterilization chamber 110 by a predetermined depth. Although various detection means can be adopted as the insertion depth detection unit, in the ultraviolet ray irradiation device 10A according to the embodiment 1, the bare skin detection unit 210 which detects a bare skin of an operator W is used as the insertion depth detection unit.

As the bare skin detection unit 210, for example, an infrared sensor can be used. The infrared sensor used in the ultraviolet ray irradiation device 10A according to the embodiment 1 is a sensor which detects an infrared ray of a wavelength emitted from an object having a temperature substantially equal to a bare skin temperature of a human out of infrared rays received in a state where the hand on which the glove G is mounted is inserted through the insertion opening 120. Accordingly, the bare skin detection unit 210 can detect the exposed bare skin. The detail of the bare skin detection unit 210 is described later.

Figure 5:
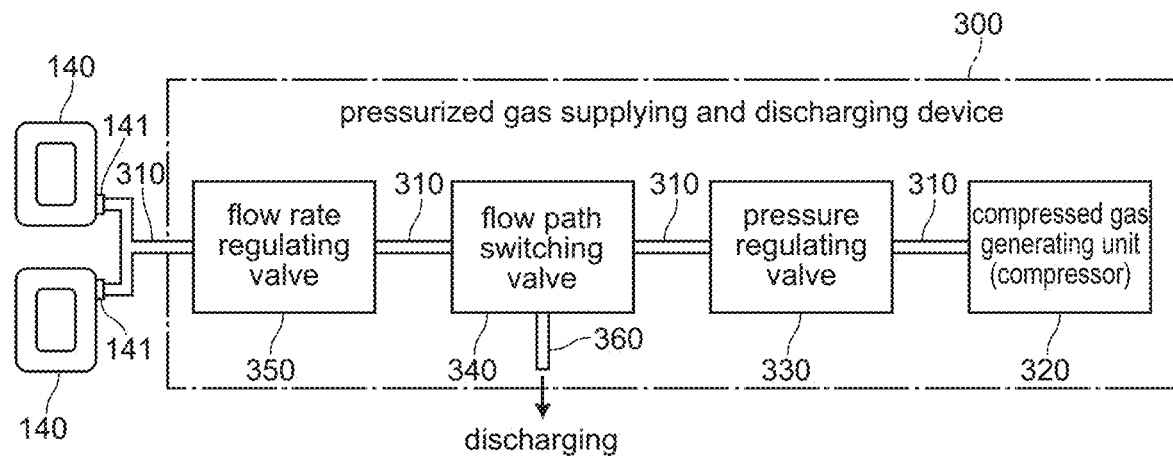
FIG. 5 is a view for describing a configuration of a pressurized as supplying and discharging device 300 of the ultraviolet ray irradiation device 10A according to the embodiment 1
Figure 6:
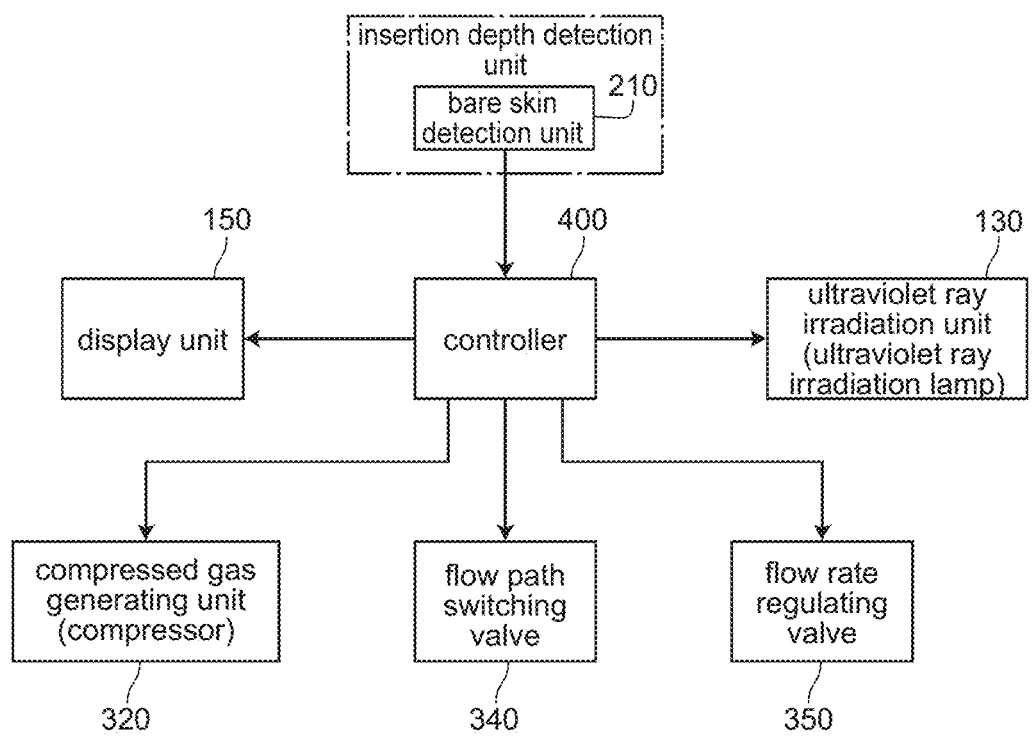
FIG. 6 is a block diagram for describing a control of the ultraviolet ray irradiation device 10A according to the embodiment 1.

As shown in FIG. 5 and FIG. 6, the ultraviolet ray irradiation device 10A according to the embodiment 1 includes: a pressurized gas supplying and discharging device 300 which supplies the gas (assuming air) under pressure to the inside of the ultraviolet ray blocking balloons 140, and discharges the gas supplied under pressure; and a controller 400 which has a function of performing a turn-on and turn-off control of the ultraviolet ray irradiation units 130 and a pressurized gas supplying and discharging control of the pressurized gas supplying and discharging device 300. The detail of the pressurized gas supplying and discharging device 300 and the controller 400 is described later.

The ultraviolet ray irradiation device 10A according to the embodiment 1 is a type where a hand on which the glove G is mounted is inserted into the sterilization chamber 110 in an upward direction from below (see FIG. 1). Accordingly, the insertion opening 120 is formed in a lower surface side of the sterilization chamber housing 100 (see FIG. 2). The insertion opening 120 has a rectangular planar shape (see FIG. 3). However, in the ultraviolet ray irradiation device 10A according to the embodiment 1, the insertion opening 120 is formed into a rectangular shape having round corner portions. Two insertion openings 120 are formed corresponding to left and right hands. To describe these two insertion openings 120 collectively, the expression "a pair of insertion openings 120" may be also adopted.

The glove G is a glove which is made of an ultraviolet ray non-transmitting material. For example, the glove G is formed using a lubber material such as nitrile or latex or thermoplastic resin which contains an ultraviolet ray interrupting material such as titanium oxide. The glove G is of a short length which covers a range from fingertips to a wrist of an operator. Accordingly, in a case where an operator wears an operation-use clothing having short sleeves, when the glove G is mounted on the hand of the operator W, although the hand of the operator h is covered by the glove G including the wrist of the operator W, a region Wa of an arm of the operator W which is not covered by the glove G is brought to a state where his/her skin is exposed.

In the glove G, assume a portion of glove G which covers the wrist of the operator W as "a wrist portion Ga of the glove G". The region Wa of the arm of the operator W which is not covered by the glove G is referred to as "a bare skin region Wa right below the wrist portion Ga of the glove G" or simply "the bare skin region Wa".

Hereinafter, the main constitutional elements of the ultraviolet ray irradiation device 10A according to the embodiment 1 are described in detail in order. First, the sterilization chamber housing 100 is described with reference to FIG. 1 and FIG. 2.

The sterilization chamber housing 100 is formed of an ultraviolet ray blocking member which blocks ultraviolet rays such as a metal plate. Two slits S1, S2 are formed at predetermined interval on a front surface of the sterilization chamber housing 100 (a surface on a side facing a face of the operator W) (see FIG. 1). A semi-transparent acrylic plate or the like to which processing which can block ultraviolet rays such as smoke processing is applied is fitted in these two slits S1, S2. With such a configuration, when the operator W inserts hands on which gloves G are mounted into the sterilization chamber 110, it is possible to check whether or not the hand on which the gloves G are mounted are inserted into the sterilization chamber 110 by a predetermined depth without being affected by ultraviolet rays. In this embodiment "a state where the hand is inserted into the sterilization chamber 110 by a predetermined depth" means "a state where the hand is inserted into the sterilization chamber 110 by a depth which enables appropriate sterilization".

The sterilization chamber housing 100 includes a sterilization chamber housing member 170. The sterilization chamber housing member 170 is mounted on the sterilization chamber housing 100, and forms one surface of the sterilization chamber housing 100. The above-mentioned insertion openings 120 are formed in the sterilization chamber housing member 170. In the ultraviolet ray irradiation device 10A according to the embodiment 1, the insertion openings 120 are formed on a lower surface side of the sterilization chamber housing 100 and hence, the sterilization chamber housing member 170 forms a bottom surface of the sterilization chamber housing 100.

A plurality of ultraviolet ray irradiation lamps 130 are mercury-arc lamps which emit ultraviolet rays having a wavelength of 185 to 280 nm. The plurality of ultraviolet ray irradiation lamp's 130 are disposed on an inner wall surface 110a of an upper surface side of the sterilization chamber 110 parallel to each other. The respective ultraviolet ray irradiation lamps 130 are disposed parallel to each other at predetermined interval. In the sterilization chamber 110, the plurality of ultraviolet ray irradiation lamps 130 extend over the substantially whole region in a width direction (x axis direction). A protective sheet 131 made of an ultraviolet ray transmitting material is disposed so as to cover the entirety of the plurality of ultraviolet ray irradiation lamps 130.

The protective sheet 131 is provided for preventing scattering of broken pieces of the ultraviolet ray irradiation lamp 130 in the sterilization chamber 110 even when the ultraviolet ray irradiation lamp 130 is broken. Although not shown in the drawings, a protective net may be disposed on a front surface of the protective sheet 131. Also, not shown in the drawings, an aluminum toil to which wrinkling is applied and which forms a reflector adheres to respective inner wall surfaces of the sterilization chamber housing 100. The aluminum Foil reflects and scatters ultraviolet rays irradiated in a direction from the ultraviolet ray irradiation lamp 130 toward the respective inner wall surfaces of the sterilization chamber 110.

Next, the insertion opening 120 and the ultraviolet ray blocking balloon 140 are described in detail with reference to FIG. 2, FIG. 3, and FIG. 4. As described previously, the insertion opening 120 is formed in the sterilization chamber housing member 170 which forms one surface of the sterilization chamber housing 100. In such a configuration, the sterilization chamber housing member 170 has a predetermined depth h in an insertion direction (a direction along the z axis) of a hand on which the glove G is mounted. Accordingly, the edge portion 121 of the insertion opening 120 has a wall surface having a height (assuming a height h) which corresponds to the depth h of the sterilization chamber housing member 170 along the insertion direction (the direction along the z axis) of the hand on which the glove is mounted. The depth h of the sterilization chamber housing member 170 preferably falls within a range of 30 mm to 70 mm. In the ultraviolet ray irradiation device 10A according to the embodiment 1, the depth h of the sterilization chamber housing member 170 is set to approximately 50 mm. Accordingly, the height h of the edge portion 121 of the insertion opening 120 is also set to approximately 50 mm.

In the ultraviolet ray irradiation device 10A according to the embodiment 1, the ultraviolet ray blocking balloon 140 having an annular shape is disposed so as to surround the edge portion 121 of the insertion opening 120 one turn along the edge portion 121. That is, the ultraviolet ray blocking balloon 140 is formed in an annular shape such that one elongated ultraviolet ray blocking balloon surrounds the edge portion 121 of the insertion opening one turn along the edge portion 121.

The ultraviolet ray blocking balloon 140 is disposed on the edge portion 121 of the insertion opening 120 more on a deep side (a sterilization chamber 110 side) of the insertion opening 120 with respect to the bare skin detection unit 210 which is an insertion depth detection unit.

A pressurized gas supplying and discharging opening 141 (see FIG. 4) is formed in the ultraviolet ray blocking balloon 140. A gas communication pipe 310 of the pressurized gas supplying and discharging device 300 is mounted on she pressurized gas supplying and discharging opening 141. The pressurized gas supplying and discharging device 300 is described later.

The ultraviolet ray blocking balloon 140 is inflated when a gas is supplied under pressure to the ultraviolet ray blocking balloon 140, and the ultraviolet ray blocking balloon 140 is deflated when the supplied gas under pressure is discharged from an inflated state. To be more specific, before a gas is supplied under pressure to the ultraviolet ray blocking balloon 140, the ultraviolet ray blocking balloon 140 forms an opening 140a (see FIG. 3 and FIG. 4) which allows the insertion and the removal of a hand on which the glove G is mounted. When the gas is supplied under pressure to the ultraviolet ray blocking balloon 140 in a state where the hand on which the glove G is mounted is inserted, the ultraviolet ray blocking balloon 140 is inflated, and surrounds a wrist portion of the glove G in a state where the ultraviolet ray blocking balloon 140 is brought into close contact with the wrist portion Ga of the glove G. Then, when the gas supplied to the ultraviolet ray blocking balloon 140 is discharged, the ultraviolet ray blocking balloon 140 is deflated and hence, the ultraviolet ray blocking balloon 140 forms the opening 140a which allows the insertion and the removal of the hand on which the glove G is mounted. The detail of this operation is described later.

Figure 3:
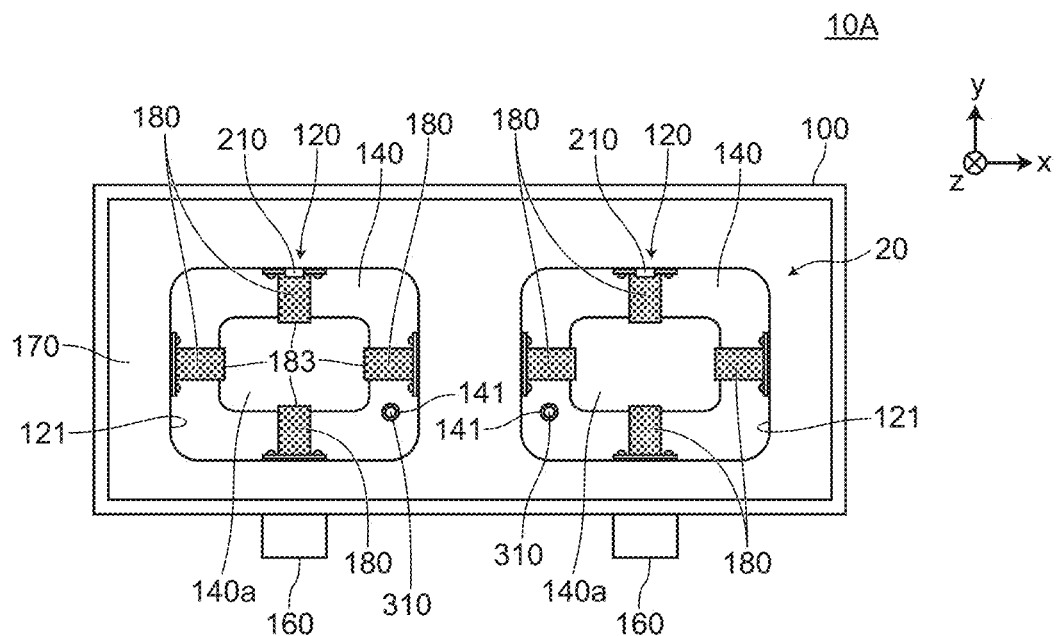
FIG. 3 is a plan view of a lower surface of the ultraviolet ray irradiation device shown in FIG. 1 as viewed in a direction indicated by an arrow z.
Figure 4:
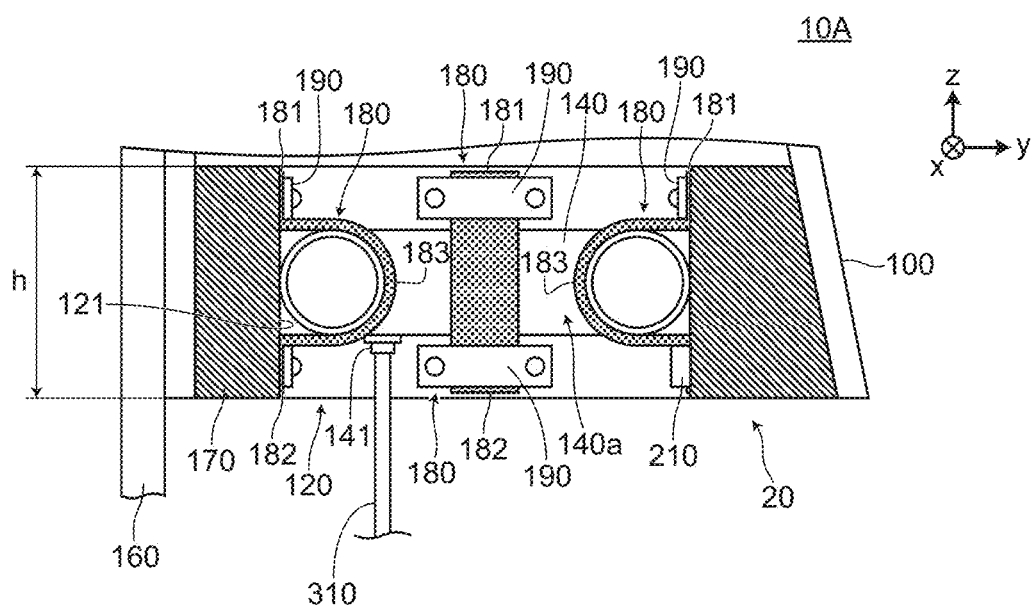
FIG. 4 is a view showing a portion of the ultraviolet ray irradiation device shown in FIG. 2 in a frame A indicated by a broken line in an enlarged manner.

The ultraviolet ray blocking balloon 140 is supported on the edge portion 121 of the insertion opening 120 by deflation assist belts 180 having stretching and shrinking property at a plurality of portions (four portions in this embodiment) (see FIG. 3 and FIG. 4). The deflation assist belt 180 is made of a material having excellent stretching and shrinking property such as synthetic rubber or natural rubber. When the ultraviolet ray blocking balloon. 140 is inflated, the deflation assist belt 180 is stretched along with the inflation of she ultraviolet ray blocking balloon 140. When the ultraviolet ray blocking balloon 140 is deflated, the deflation assist belt 180 is shrunken along with the deflation of the ultraviolet ray blocking balloon 140 so as to assist deflation of the ultraviolet ray blocking balloon 140.

The deflation assist belts 180 are mounted at four portions on the edge portion 121 of the insertion opening 120 in a circumferential direction. The deflation assist belt 180 has a U-shaped folded shape, and supports a peripheral surface of the ultraviolet ray blocking balloon 140 on an inner surface side of a folded portion 183 of the deflation assist belts 180 having the U-shaped folded shape. Both end portions 181, 182 of the deflation assist belt. 180 having the U-shaped folded shape are mounted on the edge portion 121 of the insertion opening 120.

With respect to a mounting position of the deflation assist belt 180, as shown in FIG. 3, the deflation assist belt 180 is mounted on a center portion of each side of the insertion opening 120. However, the mounting position is not limited to the center portion of each side of the insertion opening 120. Further, in FIG. 3, the case is illustrated where four portions of the ultraviolet ray blocking balloon 140 which are spaced apart from each other are supported by the deflation assist belts 180. However, the number of portions of the ultraviolet ray blocking balloon 140 to be supported by the deflation assist belts 180 is not limited to four portions, and may be less or more than four.

Various methods are considered as a method of mounting the deflation assist belt 180 on the edge portion 121 of the insertion opening 120. As one example of the method of mounting the deflation assist belt 180, the following method may be exemplified. That is, portions in the vicinity of both end portions 181, 182 of the deflation assist belt folded in a U shape are bent in an L shape thus forming L-shaped bent portions. Then, the L-shaped bent portion is sandwiched between a pressing plate 190 and the edge portion 121 of the insertion opening 120, and the pressing plate 190 is fastened to the edge portion 121 of the insertion opening 120 by screws. In the method, it may be possible to make the deflation assist belt 180 adhere to the pressing plate 190 or the edge portion 121 using an adhesive agent or the like. Accordingly, the deflation assist belt 180 can be fixed to the edge portion. 121 of the insertion opening 120 with certainty.

Subsequently, the bare skin detection unit 210 which is an insertion depth detection unit is described. As shown in FIG. 2 and FIG. 7B described later, the bare skin detection unit 210 is disposed at a position where a bare skin region right below the wrist portion Ga of the glove G can be detected when the hand on which the glove G is mounted is brought into a state where the hand is inserted into the sterilization chamber 110 by a predetermined depth. To be more specific, the bare skin detection unit 210 is mounted on the respective edge portions 121 of the pair of insertion openings 120 at a position on an entrance side of the insertion opening 120 with respect to the ultraviolet ray blocking balloon 140. The bare skin detection unit 210 outputs a bare skin detection signal as an insertion depth detection signal when the bare skin detection unit. 210 detects the bare skin region Wa right below the wrist portion Ga of the glove G.

By mounting the bare skin detection unit 210 at the above-mentioned position, when the hand on which the glove G is mounted on is brought into a state where the hand is inserted into the sterilization chamber 110 by a predetermined depth (see FIG. 7B described later), the bare skin detection unit 210 detects the bare skin region Wa right below the wrist portion Ga of the glove G, and outputs a bare skin detection signal. With respect to the hand on which the glove C is mounted, "a state where the hand is inserted into the sterilization chamber 110 by a predetermined depth" means, as described previously, a state where the hand on which the glove G is mounted is inserted into the sterilization chamber 110 to a depth which enables appropriate sterilization. Accordingly, when a bare skin detection signal is outputted from the bare skin detection unit 210, this condition indicates that the hand on which the glove G is mounted is inserted into the sterilization chamber 110 to a depth which enables appropriate sterilization.

Next, the pressurized gas supplying and discharging device 300 and the controller 400 are described with reference to FIG. 5 and FIG. 6. As shown in FIG. 5, the pressurized gas supplying and discharging device 300 includes a compressor 320 which is a compressed gas generating unit; a gas flow pipe 310 interposed between the compressor 320 and the ultraviolet ray blocking balloons 140; and a pressure regulating valve 330, a flow path switching valve 340 and a flow rate regulating valve 350 disposed on an intermediate portion of the gas flow pipe 310.

The pressure regulating valve 330 has a function of regulating a pressure of a compressed eras (also being simply expressed as "gas") generated by the compressor 320 to a predetermined pressure. With such a pressure regulating valve in supplying a gas under pressure to the ultraviolet ray blocking balloon 140, by optimizing the pressure, it is possible to prevent an excessive pressure from being applied to the ultraviolet ray blocking balloon 140, and it is possible to inflate the ultraviolet ray blocking balloon 140 with certainty. Further, by optimizing the pressure, it is possible to bring the ultraviolet ray blocking balloon 140 into close contact with the wrist of the operator W without forming a gap in conformity with a size of the wrist which differs between the individual persons. Further, in inserting the hand on which the glove G is mounted into the sterilization chamber 110, even when the wrist of the operator W moves slightly, the pressure regulating valve 330 allows the ultraviolet ray blocking balloon 140 to follow the movement of the wrist.

In the ultraviolet ray irradiation device 10A according to the embodiment 1, it is assumed that the pressure regulating valve 330 is adjusted in advance such that a gas generated by the compressor 320 becomes predetermined pressure. On the other hand, a pressure of gas which the compressor 320 generates can be reset to an optimum pressure as desired by the pressure regulating valve 330. When the pressure regulating valve is an electrically controllable pressure regulating valve, the pressure of the gas can be controlled by the controller 400 such that the pressure of the gas becomes an optimum value as desired.

The flow path switching valve 340 has a function of switching a flow direction of a gas which passes through the gas flow pipe 310 between "a flow direction on a pressurized gas supply side" where a gas is supplied under pressure to the ultraviolet ray blocking balloon 140 and "a flow direction on a pressurized gas discharge side" where the gas supplied under pressure to the ultraviolet ray blocking balloon 140 is discharged to the outside.

With such a flow path switching valve 340, when the flow direction of a gas which passes through the gas flow pipe 310 is switched to "a flow direction on a pressurized gas supply side", a gas generated by the compressor 320 (a pressure of the gas is set to a predetermined pressure by the pressure regulating valve) passes through the gas flow pipe 310, and is supplied under pressure to the ultraviolet ray blocking balloons 140 through the pressurized gas supplying and discharging openings 141. On the other hand, when the flow direction of the gas which passes through the gas flow pipe 310 is switched to "a flow direction on a pressurized gas discharge side" by the flow path switching valve 340, the gas supplied under pressure to the ultraviolet ray blocking balloons 140 passes through the gas flow pipe 310 through the pressurized gas supplying and discharging openings 141, and is discharged to the outside through a gas discharge pipe 360.

The flow rate regulating valve 350 has a function of switching a flow rate of a gas which passes through the gas flow pipe 310 between "a flow rate on a pressurized gas supply side" where the gas is supplied under pressure to the ultraviolet ray blocking balloons 140 an a "a flow rate on a pressurized gas discharge side" where the gas supplied under pressure to the ultraviolet ray blocking balloons 140 is discharged to the outside. In this case, "a flow rate on a pressurized gas supply side" is set smaller than "a flow rate on a pressurized gas discharge side". By regulating a flow rate of a gas by the flow rate regulating valve 350, it is possible to regulate an inflating speed and a deflating speed of the ultraviolet ray blocking balloon 140.

More specifically, in inflating the ultraviolet ray blocking balloon 140, the flow rate regulating valve 350 is switched to "a flow rate on a pressurized gas supply side". Then, the gas is supplied under pressure to the ultraviolet ray blocking balloon 140 at "a flow rate on a pressurized gas supply side", and the ultraviolet ray blocking balloon 140 is inflated. In such an operation, "a flow rate on a pressurized gas supply side" is a flow rate which allows the ultraviolet ray blocking balloon 140 to be inflated at a speed which does not give a discomfort or a stress to an operator.

On the other hand, in deflating the inflated ultraviolet ray blocking balloon 140, the flow rate regulating valve 350 is switched to "a flow rate on a pressurized gas discharge side". Then, the gas supplied under pressure to the ultraviolet ray blocking balloon. 140 at "a flow rate on a pressurized gas discharge side" is discharged, and the ultraviolet ray blocking balloon 140 is deflated. In this case, "a flow rate on a pressurized gas discharge side" is a flow rate which allows the ultraviolet ray blocking balloon 140 to be deflated within a time shorter than a time for inflating the ultraviolet ray blocking balloon 140 by supplying the gas under pressure to the ultraviolet ray blocking balloon 140. As an example, the flow rate is a flow rate at which the ultraviolet ray blocking balloon 140 is deflated instantaneously. In discharging the gas, it is preferable to fully open the flow rate regulating valve 350 such that a flow rate (flow speed) of the gas to be discharged becomes maximum.

In this manner, a flow rate of a gas can be switched between "a flow rate on a pressurized gas supply side" and "a flow rate on a pressurized gas discharge side" by the flow rate regulating valve 350. Accordingly, in supplying a gas under pressure to the ultraviolet ray blocking balloon 140, the ultraviolet ray blocking balloon. 140 is inflated at a speed which does not give a discomfort or a stress to an operator. On the other hand, in deflating the inflated ultraviolet ray blocking balloon 140, the inflated ultraviolet ray blocking balloon 140 is instantaneously deflated and hence, an operator is instantaneously released from a state where a wrist of the operator is surrounded by the ultraviolet rays blocking balloon 140.

A control of generation and stop of a compressed gas by the compressor 320, a switching control of a flow direction by the flow path switching valve 340 (the switching control between "a flow direction on a pressurized gas supply side" and "a flow direction on a pressurized gas discharge side"), a flow rate regulating control by the flow rate regulating valve 350 (a switching control between "a flow rate on a pressurized gas supply side" and "a flow rate on a pressurized gas discharge side") can be performed in response to a control signal transmitted from the controller 400.

The controller 400 performs an overall control of the ultraviolet ray irradiation device 10A according to the embodiment 1. Controls relating to the description of the ultraviolet ray irradiation device 10A according to the embodiment 1 are described hereinafter. In this case, controls which the controller 400 performs include, as shown in FIG. 6, controls for controlling operations of the compressor 320, the flow path switching valve 340 and the flow rate regulating valve 350 in the pressurized gas supplying and discharging device 300 (see FIG. 5), a control performed for turning on or off the ultraviolet ray irradiation lamps 130, and a control performed for displaying whether or not a hand on which the glove G is mounted is inserted into the sterilization chamber 110 by a predetermined depth on the display unit 150. These controls are performed based on a bare skin detection signal outputted from the bare skin detection unit 210. The specific controls are described later.

Next, the operation of the ultraviolet ray irradiation device 10A according to the embodiment 1 is described. In the description made hereinafter, the operation of the ultraviolet ray blocking balloon 140 and the operation of the controller 400 are mainly described.

FIG. 7A to 7C are views for describing the operation of the ultraviolet ray blocking balloon 140. In FIGS. 1A to 7C, FIG. 7A is a view showing a frame A indicated by a broken line in FIG. 2 in an enlarged manner, and shows a state where the ultraviolet ray blocking balloon 140 is deflated. FIG. 7B is a view showing a state where a hand on which the glove G is mounted is inserted into the opening 140a formed by the ultraviolet ray blocking balloon 140 in the state shown in FIG. 7A, and FIG. 7C is a view showing a state where the ultraviolet ray blocking balloon 140 is inflated from the state shown in FIG. 7B. The operation of the ultraviolet ray blocking balloon 140 shown in FIG. 7A to 7C is the operation on a side where either one of left or right hand is inserted into the opening 140a. Substantially the same operation is performed also on a side where the other hand is inserted into the opening 140a.

In an initial state, the gas is not supplied under pressure to the ultraviolet ray blocking balloon 140 so that the ultraviolet ray blocking balloon 140 takes a deflated state. Accordingly, the ultraviolet ray blocking balloon 140 forms the opening 140a which allows the insertion and removal of the hand on which the glove G is mounted (see FIG. 7A).

In the state show in FIG. 7A, the hand on which the glove C is mounted is inserted into the opening 140a formed by the ultraviolet ray blocking balloon 140 as shown in FIG. 7B. When the bare skin detection unit 210 detects the bare skin region Wa, a bare skin detection signal is transmitted to the controller 400. The controller 400, based on the bare skin detection signal transmitted from the bare skin detection unit. 210, transmits a signal which indicates the insertion of the hand on which the glove G is mounted into the sterilization chamber 110 by a predetermined depth (a depth which enables appropriate sterilization) to the display unit 150.

The display unit 150 performs a display indicating that the hand on which the glove G is mounted is inserted into the sterilization chamber 110 by the predetermined depth (depth which enables appropriate sterilization). Another display example which the display unit 150 performs, for example, the insertion of the hand is notified by turning on a blue las or generating a voice. Accordingly, an operator W knows the insertion of the hand on which the glove is mounted by the depth which enables the appropriate sterilization. Further, ode operator W can visually recognize an appearance in which the hand on which the glove G is mounted is inserted into the sterilization chamber 110 through slits S1, S2.

The controller 400 controls the flow path switching valve 340 and the flow rate regulating valve 350 respectively. That is, the controller 400 controls the flow path switching valve 340 such that the flow direction of a gas which passes through the gas flow pipe 310 becomes "a flow direction on a pressurized gas supply side" where a gas is supplied under pressure to the ultraviolet ray blocking balloon 140. The controller 400 controls the flow rate regulating valve 350 such that a flow rate of a gas supplied under pressure to the ultraviolet ray blocking balloon 140 becomes "a flow rate on a pressurized gas supply side" where the gas is supplied under pressure to the ultraviolet ray blocking balloon 140. Then, the controller 400 controls the compressor 320 so as to make the compressor 320 generate a gas. In this control, it is assumed that the pressure regulating valve 330 performs pressure regulation such that a pressure of the gas which the compressor 320 generates becomes a predetermined pressure.

In this manner, the pressure of the gas which the compressor 320 generates is regulated to the predetermined pressure by the pressure regulating valve 330. The gas passes through the flow path switching valve 340, and a flow rate of the gas is set to "a flow rate on a pressurized gas supply side" by the flow rate regulating valve 350, and the gas is supplied to the ultraviolet ray blocking balloon 140. Accordingly, the ultraviolet ray blocking balloon 140 is inflated at a speed which does not give a discomfort and a stress to the operator W, and surrounds the wrist portion Ga of the glove G in a state where the ultraviolet ray blocking balloon 140 is brought into close contact with the wrist portion Ga of the glove G as shown in FIG. 7C and FIG. 8.

Figure 8:
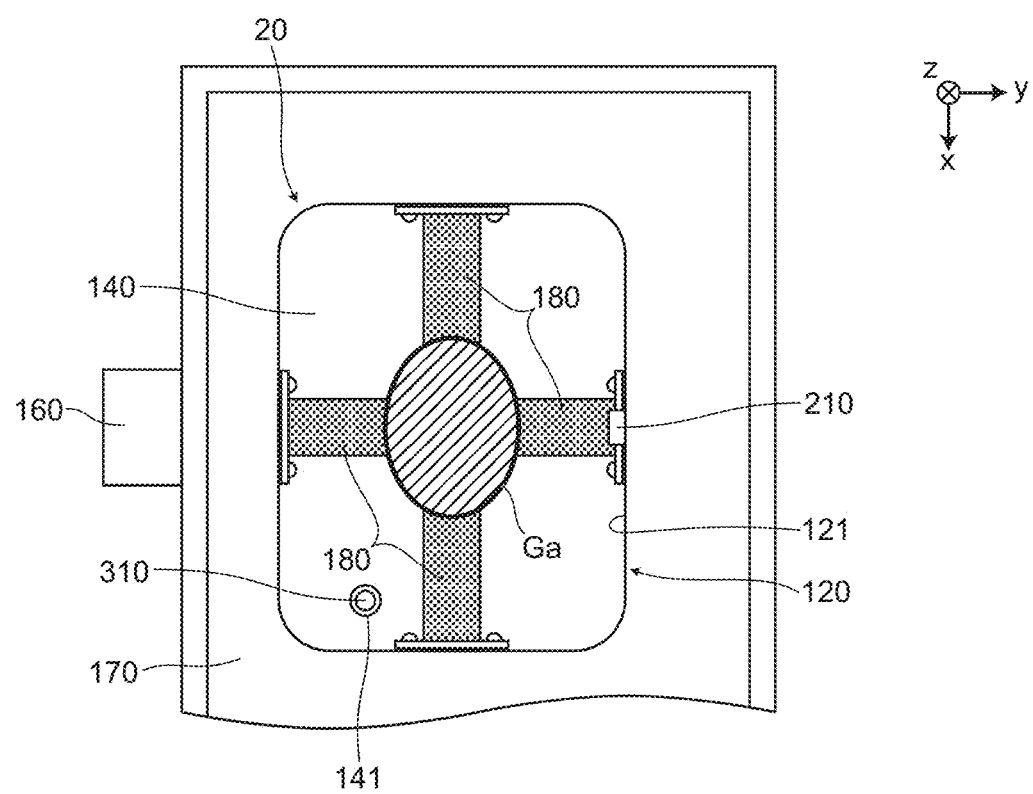

FIG. 8 is a plan view showing an appearance in which the ultraviolet ray blocking balloon. 140 surrounds the wrist portion Ga of the glove G in a state where the ultraviolet ray blocking balloon 140 is brought into close contact with the writ portion Ga of the glove G as viewed in a direction indicated by an arrow z. As shown in FIG. 8, the state on a side of either one of left or right hand is shown. However, also on a side of the other hand, in the same manner, the ultraviolet ray blocking balloon 140 surrounds the wrist portion Ga of the glove G in a state where the ultraviolet ray blocking balloon 140 is brought into close contact with the wrist portion Ga of the glove G.

In inflating the ultraviolet ray blocking balloon 140, the deflation assist belts 180 extend along with the inflation of the ultraviolet ray blocking balloon 140 time from a point of time that the ultraviolet ray block log balloon 140 starts inflation to a point of time that the ultraviolet ray blocking balloon 140 surrounds the wrist portion Ga of the glove C in a state where the ultraviolet ray blocking balloon 140 is brought into close contact with the wrist portion Ga of the glove G (referred to as an inflation time) is approximately 2 seconds. The inflation time can be properly set by regulating "a flow rate on a pressurized gas supply side" using the flow rate regulating valve 354.

When the ultraviolet ray blocking balloon. 140 starts inflation and, then, surrounds the wrist portion Ga of the glove G in a state where the ultraviolet ray blocking balloon. 140 is brought into close contact with the wrist portion Ga. of the glove G, the controller 400 turns on the ultraviolet ray irradiation lamps 130. That is, the controller 400 performs a control in which the ultraviolet ray irradiation lamps 130 are turned on after a lapse of the inflation time. It is preferable that the operator W opens respective fingers of the hand on which the glove G is mounted after the hand is inserted into the sterilization chamber 110 as shown in FIG. 7B.

When the ultraviolet ray irradiation lamps 130 are turned on, the surface of the glove G can be sterilized. At this stage of operation, as shown in FIG. 7A to FIG. 7C and FIG. 8, the ultraviolet ray blocking balloon 140 surrounds the wrist portion Ga of the glove C in a state where the ultraviolet ray blocking balloon 140 is brought into close contact with the wrist portion Ga of the glove G. Accordingly, ultraviolet rays irradiated by the ultraviolet ray irradiation lamps 130 are blocked by the ultraviolet ray blocking balloon 140 with certainty. Therefore, it is possible to prevent with certainty leaking of the ultraviolet rays to the outside of the sterilization chamber housing 100. As a result, as shown in FIG. 7C, even when a bare skin region ha exists on the operator W, it is possible to prevent with certainty the irradiation of the ultraviolet rays to the bare skin region ha. Further, it is possible to prevent with certainty the irradiation of the ultraviolet rays not only to the operator who is performing sterilization at the moment but also to operators around such an operator.

It is preferable that the controller 400 perform a preheating control at a stage before the ultraviolet ray irradiation lamps 130 are turned on. In this case, it is possible to preheat the ultraviolet ray irradiation lamps 130 by making use of the inflation time of approximately G seconds from the point of time that the ultraviolet ray blocking balloon 140 starts inflation to a point of time that the ultraviolet ray blocking balloon 140 is brought into a state where the ultraviolet ray blocking balloon 140 surrounds the wrist portion of the glove in a state where the ultraviolet ray locking balloon 140 is brought into close contact with the wrist portion of the glove. To be more specific, the controller 400 performs a control in which preheating of the ultraviolet say irradiation lamps 130 is started simultaneously with a control for inflating the ultraviolet ray blocking balloon 140, and performs a control in which the ultraviolet ray irradiation lamps 130 are turned on after a lapse of the inflation time of approximately 2 seconds after starting preheating.

In this manner, by performing preheating of approximately seconds before the ultraviolet ray irradiation lamps 130 are turned on, a rise time at the time of turning on the ultraviolet ray irradiation lamps 130 can be shortened. Accordingly, an efficient sterilization operation can be performed thus extending a lifetime of the ultraviolet ray irradiation lamps 130.

By turning on the ultraviolet ray irradiation lamps 130 in this manner, the glove G can be sterilized by the irradiation of the ultraviolet rays on the hand on which the glove G is mounted. A time from a point of time that the ultraviolet ray blocking balloon 140 starts inflation to a point of time that the sterilization is completed is approximately 5 to 8 seconds.

Then, the controller 400 turns off the ultraviolet ray irradiation lamps 130, controls the compressor 320 so as to make the compressor 320 and stop the generation of the compressed gas, and controls the flow rate regulating valve 350 such that the flow rate of the gas becomes "a flow rate on a pressurized gas discharge side". In such a control, preferable that the control of the flow rate regulating valve 350 such that the flow rate of the gas becomes "a flow rate on a pressurized gas discharge side" specifically mean a control where the flow rate regulating valve 350 is fully opened. By fully opening the flow rate regulating valve 350, a gas supplied under pressure to the ultraviolet ray blocking balloon 140 is discharged at a maximum flow rate (maximum speed) and hence, the ultraviolet ray blocking balloon 140 is deflated instantaneously.

When the ultraviolet ray blocking balloon 140 is deflated, the deflation assist belts 180 also shrink along with the deflation of the ultraviolet ray blocking balloon 140. In this case, the deflation assist belts 180 hold the ultraviolet ray blocking balloon 140 at four portions (respective center portions of four sides) as shown in FIG. 3 and hence, the deflation assist belts 180 shrink at four portions whereby the deflation assist belts 180 can uniformly assist the deflation of the ultraviolet ray blocking balloon 140 at respective sides. Accordingly, the ultraviolet ray blocking balloon 140 returns to an initial state (a state before the gas is supplied under pressure to the ultraviolet ray blocking balloon 140) shown in FIG. 7A, and Forms the opening 140a which allows the insertion and the removal of the hand on which the glove G is mounted. Therefore, the operator W is released from a state where the ultraviolet ray blocking balloon 140 is brought into close contact with the wrist portion of the hand of the operator W and hence, the operator W can remove the hand on which the glove G is mounted from the opening 140a of the ultraviolet ray blocking balloon 140.

As described above, according to the ultraviolet ray irradiation device 10A according to the embodiment 1, when the hand on which the glove G is mounted is inserted into the sterilization chamber 110 by a predetermined depth, that is, a depth which enables the appropriate sterilization, the ultraviolet ray blocking balloon 140 is inflated and surrounds the wrist portion Ga of the glove G in a state where the ultraviolet ray blocking balloon 140 is brought into close contact with the wrist portion. Ga. Accordingly, a sterilization object region (a region of the hand on which the glove G is mounted) which exists in the sterilization chamber 110 and a bare skin region Wa of the operator W are partitioned from each other with certainty by the ultraviolet ray blocking balloon 140. The ultraviolet ray irradiation lamps 130 are turned on in such a state and hence, it is possible to prevent with certainty the irradiation of the ultraviolet rays to the bare skin region Wa of the operator W. Further, it is also possible to prevent with certainty the irradiation of the ultraviolet rays not only to the operator who performs sterilization at the moment but also operators around the operator.

Further, in the ultraviolet ray irradiation device 10A according to the embodiment. 1, the bare skin detection unit 210 which detects a bare skin of the operator is used as the insertion depth detection unit. The bare skin detection unit 210 is disposed at the position where the bare skin region Wa right below the wrist portion Ga of the glove G can be detected when the hand on which the glove G is mounted is brought into a state where the hand is inserted into the sterilization chamber 110 through the insertion opening 120 by a predetermined depth. Accordingly, in a case where the glove G is a glove of a type having a short length which covers a range from the fingertips to the wrist of the operator W, when the hand on which the glove G is mounted is brought into a state where the hand is inserted into the sterilization chamber 110 by a predetermined depth, the bare skin region ha of the operator W (the bare skin region ha right below the wrist portion Ga. of the glove G) is detected. Therefore, it is possible to detect that the hand on which the glove G is mounted is brought into a state where the hand is inserted into the sterilization chamber 110 by the predetermined depth.

In the ultraviolet ray irradiation device 10A according to the embodiment 1, in inflating the ultraviolet ray blocking balloon 140, the ultraviolet ray blocking balloon 140 is inflated by supplying a gas under pressure in a state where a flow rate (speed) of the gas supplied under pressure to the ultraviolet ray blocking balloon 140 is suppressed. Accordingly, the ultraviolet ray blocking balloon 140 is inflated at a speed which does not give a discomfort and a stress to the operator W. Further, in deflating the ultraviolet ray blocking balloon 110 in an inflated state, the ultraviolet ray blocking balloon. 140 is deflated such that a flow rate of a gas discharged from the ultraviolet ray blocking balloon 140 becomes a maximum flow rate. Therefore, after the sterilization is completed, the operator W can immediately remove the hand on which the clove G is mounted from the sterilization chamber 110.

In the ultraviolet ray irradiation device 10A according to the embodiment 1, the ultraviolet ray blocking balloon 140 is supported by the deflation assist belts 180 made of a material having excellent stretching and shrinking property such as rubber at a plurality of portions disposed at a predetermined interval. Accordingly, in deflating the ultraviolet ray blocking balloon 140 in an inflated state, the deflation assist belts 180 shrink along with the deflation of the ultraviolet ray blocking balloon 140 and hence, the deflation assist belts 180 can assist the deflation of the ultraviolet ray blocking balloon 140. As a result, the ultraviolet ray blocking balloon 140 can be deflated with certainty.

In the ultraviolet ray irradiation device 10A according to the embodiment 1, an infrared sensor is used as the bare skin detection unit 210, and a bare skin temperature of the operator W is detected by the infrared sensor, and a bare skin is detected based on a result of the detection. However, a detection unit which detects a human skin using a color sensor may be adopted in place of the infrared sensor. To be more specific, by using the color sensor which outputs a detection signal when the color sensor detects a skin color of a human or a color close to a skin color, in a case where the glove G has color other than a skin color (for example, blue or the like), when a state is brought about where the hand on which the glove G is mounted is inserted into the sterilization chamber 110 (see FIG. 7B), she color sensor used as the bare skin detection unit 210 can detect the bare skin region ha of the operator W. Also in this case, it is possible to detect that the hand on which the glove G is mounted is inserted into the sterilization chamber 110 by a predetermined depth.

Embodiment 2

Figure 9:
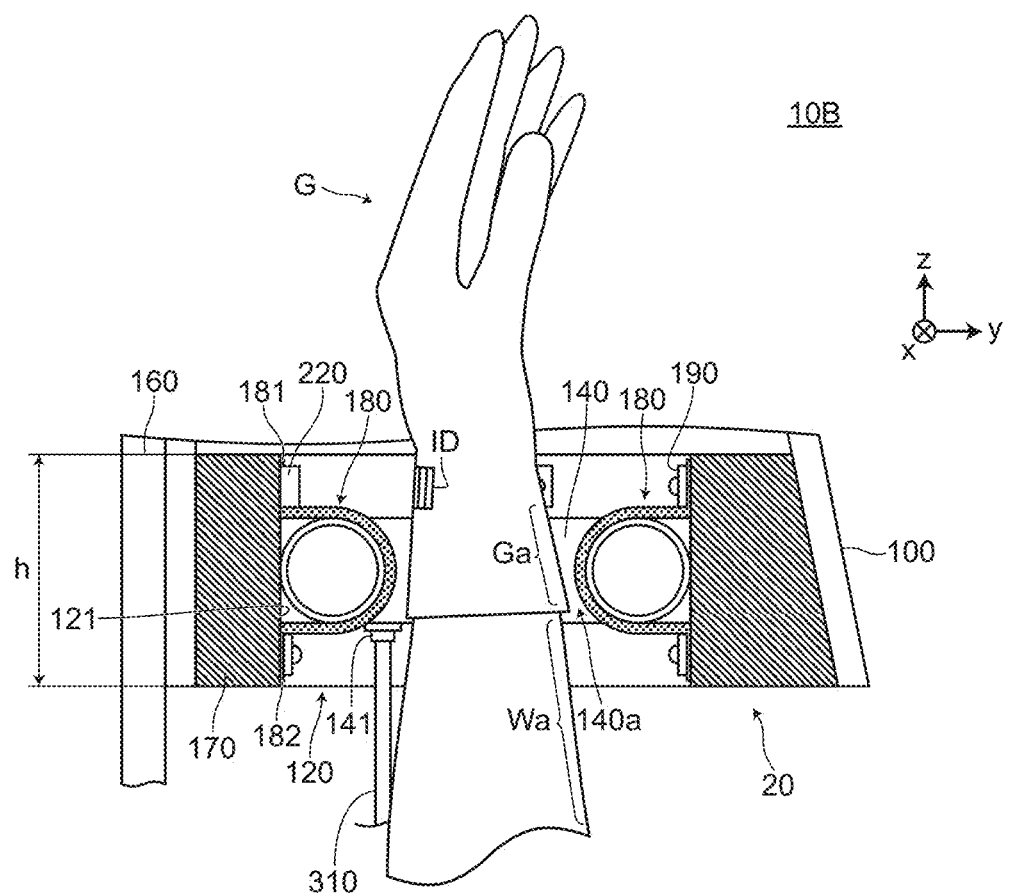
FIG. 9 is a view for describing an ultraviolet ray irradiation device 10B according to an embodiment 2.

FIG. 9 is a view for describing an ultraviolet ray irradiation device 10B according to an embodiment 2. FIG. 9 shows a state where a hand on which a glove G is mounted is inserted through an insertion opening 120 of the ultraviolet ray irradiation device 10B according to the embodiment 2. FIG. 9 corresponds to FIG. 7B used in the description of the ultraviolet ray irradiation device 10A according to the embodiment 1.

Figure 10:
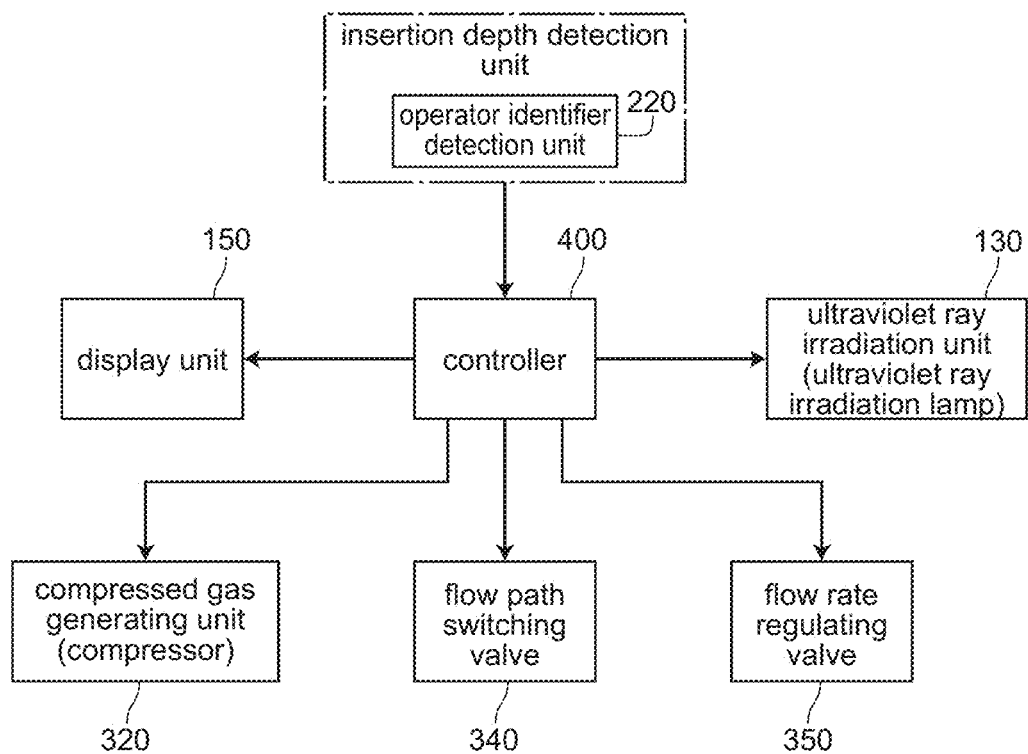
FIG. 10 is a block diagram for describing a control of the ultraviolet ray irradiation device 103 according to the embodiment 2.

FIG. 10 is a block diagram for describing a control of the ultraviolet ray irradiation device 10B according to the embodiment 2.

The ultraviolet ray irradiation device 10B according to the embodiment 2 differs from the ultraviolet ray irradiation device 10A according to the embodiment 1 with respect to an insertion depth detection unit. In the ultraviolet ray irradiation device 103 according to the embodiment 2, an operator identifier detection unit 220 which detects an operator identifier ID for identifying an operator is used as an insertion depth detection unit. As the ultraviolet ray irradiation device, there exists an ultraviolet ray irradiation device having a function where an operator identifier ID such as a bar code or a matrix-type two-dimensional code is attached to a wrist portion Ga of a glove G, an operator is identified by detecting the operator identifier ID, and sterilization states of individual operators and the like are recorded. In such an ultraviolet ray irradiation device, the operator identifier detection un t. 220 disposed in the ultraviolet ray irradiation device can be used as an insertion depth detection unit.

The operator identifier detection unit 220 is disposed at a position where the operator identifier ID cannot be detected when the hand on which the glove G is mounted is brought into a state where the hand is inserted into a sterilization chamber 110 at a shallow depth, and the operator identifier ID can be detected when the hand on which the glove G is mounted is brought into a state where the hand is inserted into the sterilization chamber 110 by a predetermined depth, that is, a depth which enables appropriate sterilization. Then, when the operator identifier ID is detected, the operator identifier detection unit 220 outputs an operator identifier detection signal as an insertion depth detection signal.

In the ultraviolet ray irradiation device 10B according to the embodiment 2, assume that the operator identifier ID is attached on a portion of the wrist portion Ga of the glove G close to a back of a hand of the operator. As shown in FIG. 9, the operator identifier detection unit 220 is disposed on a portion of the insertion opening 120 close to an entrance of the sterilization chamber 110. Accordingly, in a state where the hand on which the glove G is mounted is inserted into the sterilization chamber 110 (see FIG. 2) (see FIG. 9), when the operator identifier ID attached to the glove G is detected by the operator identifier detection unit. 220, it is safe to say that the hand on which the glove G is mounted is in a state where the hand is inserted into the sterilization chamber 110 by a predetermined depth, that is, a depth which enables appropriate sterilization.

In this manner, in the ultraviolet ray irradiation device 10B according to the embodiment 2, the operator identifier detection unit 220 is used as an insertion depth detection unit. The ultraviolet ray irradiation device 10B according to the embodiment 2 differs from the ultraviolet ray irradiation device 10A according to the embodiment 1 at this point in configuration. Accordingly, the external configuration of the ultraviolet ray irradiation device 10B and the configuration in the sterilization chamber housing 100 and, further, the configuration of a pressurized gas supplying and discharging device 300 according to the embodiment 2 are substantially equal to the corresponding configurations of the ultraviolet ray irradiation device 10A according to the embodiment 1 and hence, the repeated drawings and description are omitted as much as possible.

Hereinafter, the ultraviolet ray irradiation device 10B according to the embodiment 2 is described in the ultraviolet ray irradiation device 10B according to the embodiment 2, as shown in FIG. 10, a controller 400 uses an operator identifier detection signal transmitted from the operator identifier detection unit 220 used as the insertion depth detection unit as an insertion depth detection signal, and based on the operator identifier detection signal, operates an ultraviolet ray blocking balloon 140 as shown in FIG. 7A to FIG. 7C by controlling the pressurized gas supplying and discharging device 300 (see FIG. 5), and performs a turn-on and turn-off control of ultraviolet ray irradiation lamps 130.

The control of the pressurized gas supplying and discharging device 300 (see FIG. 5) and the control of the ultraviolet ray irradiation lamps 130 which the controller 400 performs based on an operator identifier detection signal transmitted from the operator identifier detection unit 220 are substantially equal to the control which the controller 400 performs based on a bare skin detection signal in the ultraviolet ray irradiation device 10A according to the embodiment 1. Accordingly, the description of the control of the pressurized gas supplying and discharging device 300 and the control of the ultraviolet ray irradiation lamps 130 in the ultraviolet ray irradiation device 10B according to the embodiment 2 is omitted.

As described above, to the ultraviolet ray irradiation device 10B according to the embodiment 2, the operator identifier detection unit 220 which detects the operator identities ID is used as the insertion depth detection unit. The operator identifier detection unit 220, when the hand on which the glove G is mounted is inserted through the insertion opening 120, detects that the hand on which the glove G is mounted is brought into a state where the hand is inserted into the sterilization chamber 110 by a predetermined depth (a depth which enables appropriate sterilization), and can output an operator identifier detection signal as an insertion depth detection signal. On the other hand, the controller 400 performs a control of the pressurized gas supplying and discharging device 300 and a turn-on control of the ultraviolet ray irradiation lamps 130 based on the operator identifier detection signal (insertion depth detection signal) outputted from the operator identifier detection unit 220. The control of the pressurized gas supplying and discharging device 300 and the turn-on control of the ultraviolet ray irradiation lamps 130 are substantially equal to the corresponding controls in the ultraviolet ray irradiation device 10A according to the embodiment 1.

In the ultraviolet ray irradiation device 100 according to the embodiment. 2, assume that, as shown in FIG. 9, the operator identifier ID is attached on a portion of the wrist portion Ga of the glove G close to a back of the hand of the operator, and the operator identifier detection unit 220 is disposed on a portion of the sterilization chamber 110 close to an entrance of the sterilization chamber 110. However, the ultraviolet ray irradiation de ice 100 according to the embodiment 2 is not limited to such a configuration. That is, the relationship between the attaching position of the operator identifier ID on the glove and the position of the operator identifier detection unit 220 which detects the operator identifier ID may be set such that the operator identifier ID can be detected by the operator identifier detection unit 220 when the hand on which the glove G is mounted is brought into a state where the hand is inserted into the sterilization chamber 110 by a predetermined depth (a depth which enables appropriate sterilization).

Embodiment 3

Figure 11:
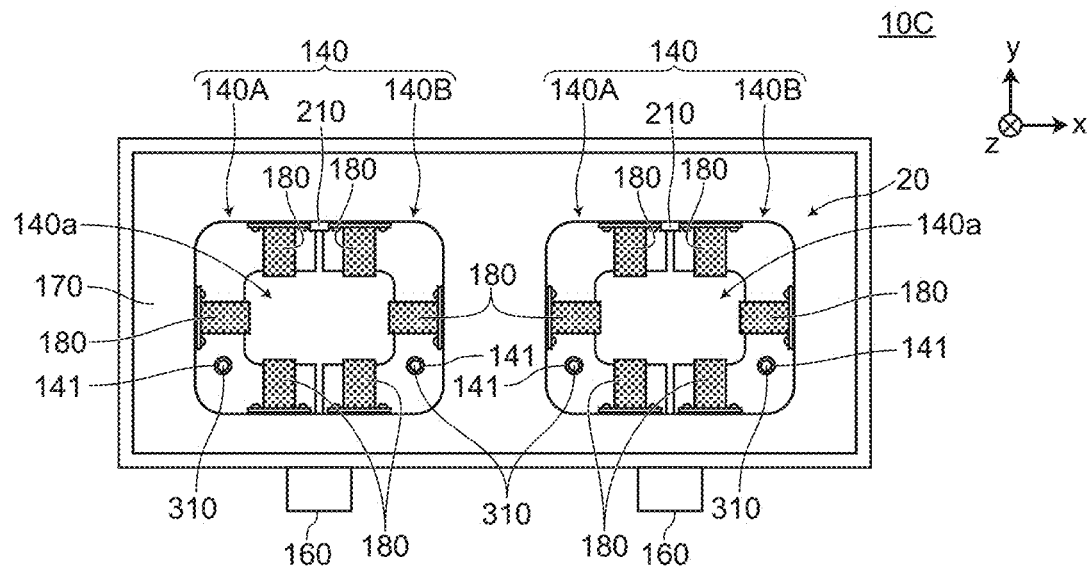
FIG. 11 is a view for describing an ultraviolet say irradiation device 10C according to the embodiment. 3.

FIG. 11 is a view for describing an ultraviolet ray irradiation device 10C according to an embodiment 3. FIG. is a view which corresponds to FIG. 3 used in the description of the ultraviolet ray irradiation device 10A according to the embodiment 1.

The ultraviolet ray irradiation device 10C according to the embodiment 3 differs from the ultraviolet ray irradiation device 10A according to the embodiment 1 and the ultraviolet ray irradiation device 10B according to the embodiment 2 with respect to respective ultraviolet ray blocking balloons 140 which correspond to left and right hands. That is, in the ultraviolet ray irradiation device 10A according to the embodiment 1 and the ultraviolet ray irradiation device 10B according to the embodiment. 2, the ultraviolet ray blocking balloon 140 is formed in an annular shape such that one elongated ultraviolet ray blocking balloon 140 surrounds an edge portion 121 of the insertion opening one turn along the edge portion 121.

On the other hand, in the ultraviolet ray irradiation device 100 according to the embodiment 3, the ultraviolet ray blocking balloon 140 is formed of a plurality of (two) ultraviolet ray blocking balloons 140A, 140B. These two ultraviolet ray blocking balloons 140A, 140B are arranged in a longitudinal row so as to surround an edge portion 121 of an insertion opening 120 one turn along the edge portion 121.

As a pressurized gas supplying and discharging device in the ultraviolet ray irradiation device 100 according to the embodiment 3, the pressurized gas supplying and discharging device 300 shown in FIG. 5 can be used. However, in the ultraviolet ray irradiation device 100 according to the embodiment 3, the ultraviolet ray blocking balloon 140 is formed of two ultraviolet ray blocking balloons 140A, 140. Accordingly, although not shown in the drawing, a gas flow pipe 310 is disposed between each of two ultraviolet ray blocking balloons 140A, 140B and a flow rate regulating valve 350. As a controller 400, the controller 400 shown in FIG. 6 or FIG. 10 can be used.

The ultraviolet ray blocking balloons 140A, 140k in the ultraviolet ray irradiation device 10C according to the embodiment 3 performs operations substantially equal to the operations shown in FIG. 1A to FIG. 7C. However, in the ultraviolet ray irradiation device 10C according to the embodiment 3, the ultraviolet ray blocking balloon. 140 is formed of two ultraviolet ray blocking balloons 140A, 140B and hence, two ultraviolet ray blocking balloons 140A, 140k perform inflation and deflation. When two ultraviolet ray blocking balloons 140A, 140k are inflated, two ultraviolet ray blocking balloons 140A, 140k are simultaneously inflated, and two ultraviolet ray blocking balloons 140A, 140B surround a wrist Ga in a state where two ultraviolet ray blocking balloons 140A, 140k are brought into close contact with the wrist portion Ga. of a glove G. When two ultraviolet ray blocking balloons 140A, 140k are deflated, two ultraviolet ray blocking balloons 140A, 140k are simultaneously deflated.

In this manner, even when the left and right ultraviolet ray blocking balloons 140 are each formed of two ultraviolet ray blocking balloons 140A, 140B, in the same manner as the above mentioned respective embodiments, it is possible to prevent with certainty the irradiation of ultraviolet rays irradiated from the ultraviolet ray irradiation lamps 130 to a bare skin region Wa of an operator W.

In FIG. 11, two ultraviolet ray blocking balloons 140A, 140B which form the ultraviolet ray blocking balloon 140 are split in two in a lateral direction (a direction along art x axis). However, the configuration may be adopted where the ultraviolet ray blocking balloon 140 is split in two in a longitudinal direction (a direction along a y axis). Splitting of the ultraviolet ray blocking balloon 140 is not limited to splitting in two and may be splitting in three or more.

[Embodiment of Ultraviolet Ray Blocking Unit]

Subsequently, an ultraviolet ray blocking unit according to the present invention is described based on an embodiment described below. In this embodiment, the ultraviolet ray blocking unit 20 according to the embodiment is described with reference to FIG. 2 to FIG. 4 used in the description of the ultraviolet ray irradiation device 10A according to the embodiment 1 described previously.

Figure 2:
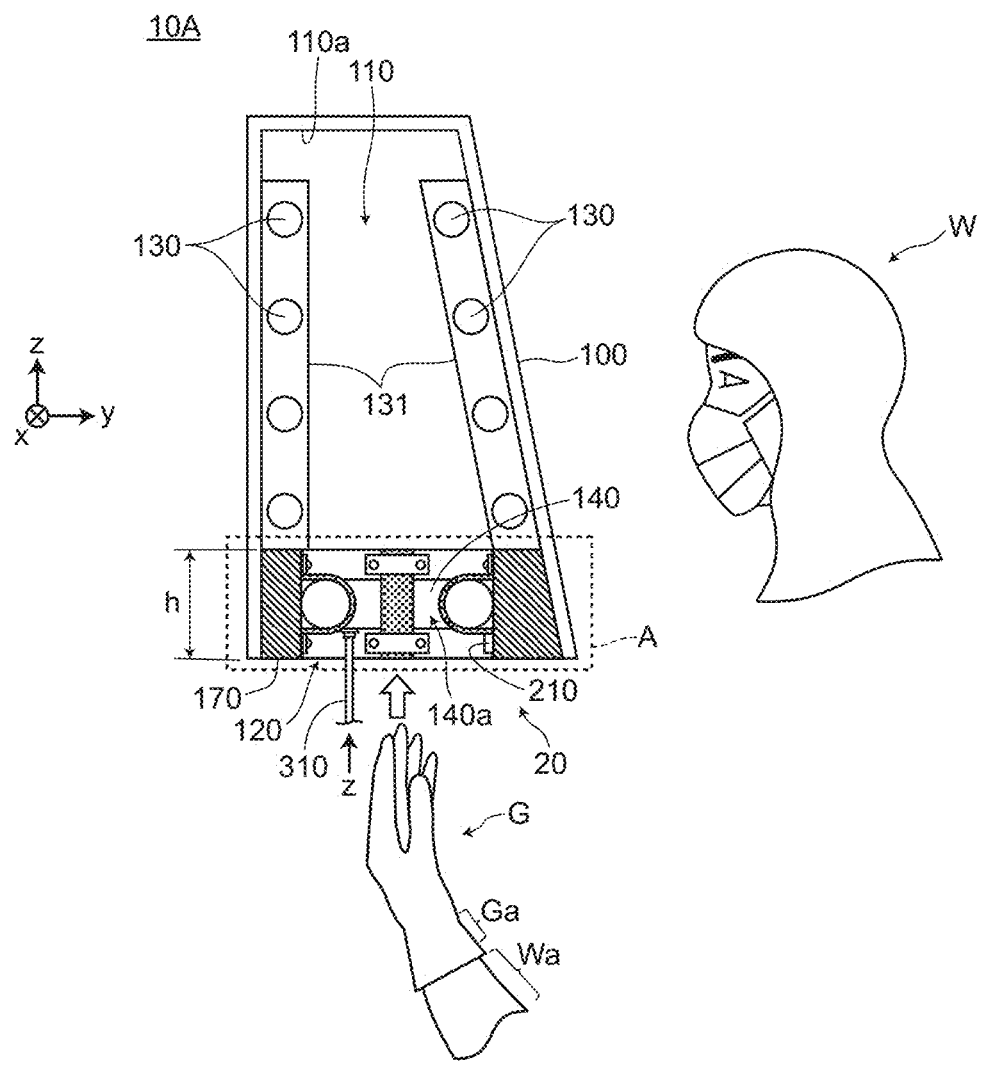
FIG. 2 is a longitudinal cross-sectional view of a side surface of the ultraviolet say irradiation device shown in FIG. 1 as viewed in a direction indicated by an arrow x.

The ultraviolet ray blocking unit 20 according to the embodiment is, as shown in FIG. 2 to FIG. 4, formed of the sterilization chamber housing member 170 and the ultraviolet ray blocking balloons 140 disposed along the edge portions 121 of the insertion openings 120 formed in the sterilization chamber housing member 170. The sterilization chamber housing member 110 forms one surface of the sterilization chamber housing 100 when the sterilization chamber housing member 170 is mounted on the sterilization chamber housing 100. In the ultraviolet ray irradiation device 10A according to the embodiment 1 shown in FIG. 2 to FIG. 4, the sterilization chamber housing member 170 forms the bottom surface of the sterilization chamber housing 100.

The ultraviolet ray blocking unit 20 having such a configuration detachably (mountable and removable) mounted on the sterilization chamber housing 100. That is, the sterilization chamber housing member 170 which is one of constitutional elements of the ultraviolet ray blocking unit is detachably mounted on the sterilization chamber housing 100 and hence, the ultraviolet ray blocking unit. 20 is also detachably mounted on the sterilization chamber housing 100. The ultraviolet ray blocking balloon 140 is supported by the deflation assist belts 180 along the edge portion 121 of the insertion opening 120. Accordingly, the deflation assist belts 180 may be also included as the constitutional elements of the ultraviolet ray blocking unit 20.

In mounting the ultraviolet ray blocking unit 20 on the sterilization chamber housing 100, the ultraviolet ray blocking unit 20 is inserted into the sterilization chamber housing 100 from below the sterilization chamber housing 100, and the ultraviolet ray blocking unit 20 is fixed to the sterilization chamber housing 100 by a fixing means such as screws (not shown in the drawings). On the other hand, in removing the ultraviolet ray blocking unit 20 from the sterilization chamber housing 100, a fixing means such as screws or the like which fix the ultraviolet ray blocking unit 20 is removed, and the ultraviolet ray blocking unit 20 is pulled out in a downward direction. Accordingly, the ultraviolet ray blocking unit. 20 can be easily mounted on the sterilization chamber housing 100 and can be easily removed from the sterilization chamber housing 100.

The bare skin detection unit 210 which is an insertion depth detection unit is disposed on the edge portion 121 of the insertion opening 120. Accordingly, when the ultraviolet ray blocking unit 20 is removed from the sterilization chamber housing 100, the bare skin detection unit 210 is also removed. In this case, by detachably mounting the bare skin detection unit 210 on the edge portion 121 oil the insertion opening 120, when the ultraviolet ray blocking unit 20 is exchanged, the bare skin detection unit. 210 can be also used for a new ultraviolet ray blocking unit 20.

Although the ultraviolet ray blocking unit 20 has been described with reference to FIG. 2 to FIG. 1 used in the description of the ultraviolet ray irradiation device 10A according to the embodiment 1 described previously. However, also in the ultraviolet ray irradiation devices 10B, according to other embodiments, the ultraviolet ray blocking unit 20 may be formed of the sterilization chamber housing member 110 and the ultraviolet ray blocking balloons 140 disposed along the edge portions 121 of the insertion openings 120 formed in the sterilization chamber housing member 170.

In the ultraviolet ray blocking unit 20 exemplified in FIG. 2 to FIG. 4, the ultraviolet ray blocking unit 20 is inserted into and fixed to the sterilization chamber-housing 100. However, the present invention is not limited to such a configuration. For example, the ultraviolet ray blocking unit 20 may be mounted on a dower end of the sterilization chamber housing 100. Such a configuration is also included in the ultraviolet ray blocking unit 20 according to the embodiment.

According to the ultraviolet ray blocking unit 20 of the embodiment, the ultraviolet ray blocking unit 20 is detachably mounted on the sterilization chamber housing 100. So, when the ultraviolet ray blocking balloon 140 is deteriorated or broken, an entirety of the ultraviolet ray blocking unit 20 can be exchanged. Therefore, maintenance of the ultraviolet ray irradiation device 10A can be easily performed.

The present invention is not limited to the above-mentioned embodiments, and various modifications can be carried out without departing from the gist of the present invention. For example, the following modifications can be carried out.

Figure 12:
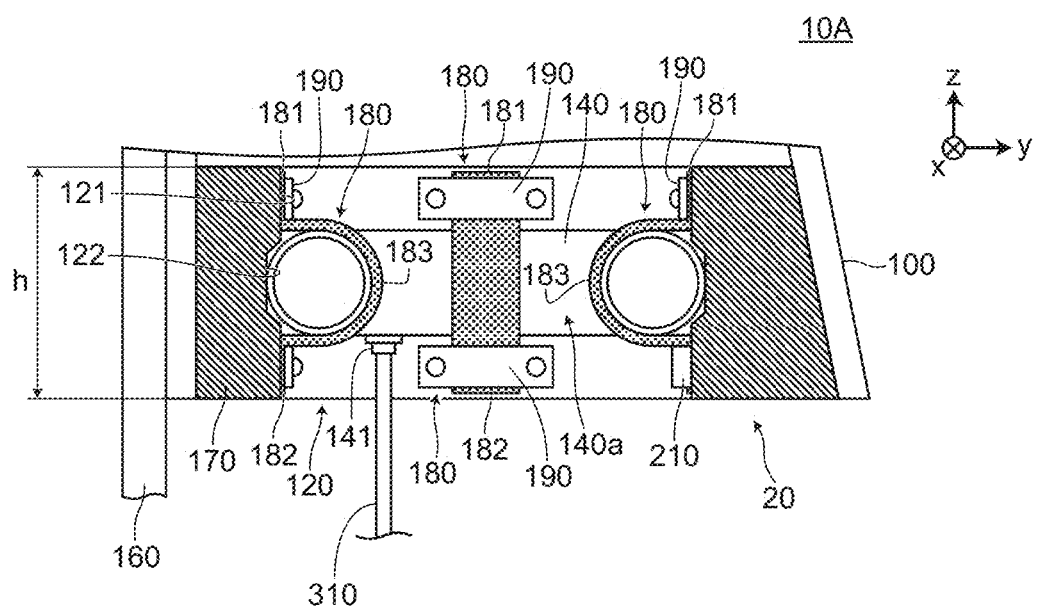
FIG. 12 is a view for describing a modification of the ultraviolet ray irradiation devices 10A, 10B, and 102 of the respective embodiments.

(1) FIG. 12 is a view for describing a modification of the ultraviolet ray irradiation devices 10A, 10B, and 10C of the respective embodiments described previously. FIG. 12 corresponds to FIG. 4 used in the description of the ultraviolet ray irradiation device 10A according to the embodiment 1. As shown in FIG. 12, a groove 122 having a concave shape is formed on an edge portion 121 of an insertion opening 120 so as to extend along the edge portion 121 one turn in a circumferential direction. A surface of an ultraviolet ray blocking balloon 140 on a side along the edge portion 121 of the insertion opening 120 is accommodated in the groove 122 having a concave shape. With such a configuration, the ultraviolet ray blocking balloon 140 can be held in a stable state by the groove 122 having a concave shape. Accordingly, in the inflation and deflation of the ultraviolet ray blocking balloon. 140, the position (particularly, the position in the vertical direction along the z axis) of the ultraviolet ray blocking balloon 140 is minimally displaced and hence, it is possible to perform inflating and deflating operation in a stable manner.

Also in the modification shown in FIG. 12, the ultraviolet ray blocking unit 20 can be formed of the sterilization chamber housing member 170 and the ultraviolet ray blocking balloons 140 disposed along the edge portions 121 of the insertion openings 120 formed in the sterilization chamber housing member 170.

(2) The insertion depth detection unit which detects that the hand on which the glove G is mounted is inserted into the sterilization chamber 110 by a predetermined depth is formed of the bare skin detection unit 210 in the ultraviolet ray irradiation device 10A according to the embodiment 1, and is formed of the operator identifier detection unit 220 in the ultraviolet ray irradiation device 10B according to the embodiment 2. However, various modifications can be carried out with respect to the insertion depth detection unit. The following (a) to (d) show such modifications of the insertion depth detection unit.

(a) In the first modification of the insertion depth detection unit, an insertion restricting unit (not shown in the drawings) which restricts an insertion depth of a hand on which a glove G is mounted is disposed in the sterilization chamber 110, and a touch sensor is mounted on the insertion restricting unit. Then, the touch sensor detects that a predetermined portion (for example, fingertip of any one of five fingers or a valley portion formed between two fingers disposed adjacently to each other) of the hand on which the glove G is mounted touches the insertion restricting unit, and outputs an insertion depth detection signal. Then, the controller 400 performs a control of the respective constitutional elements of the pressurized gas supplying and discharging device 300 and a control of the ultraviolet ray irradiation lamps 130 described in the above-mentioned respective embodiments based on the insertion depth detection signal outputted from the touch sensor.

(b) In a second modification of the insertion depth detection unit, a camera (not shown in the drawings) is disposed in the sterilization chamber 110, and a hand on which a glove G is mounted is photographed when the hand on which the glove G is mounted is inserted into the sterilization chamber 110. Then, the insertion depth detection unit detects that the hand on which the glove G is mounted is inserted into the sterilization chamber 110 by a predetermined depth based on a photographed image photographed by the camera, and outputs an insertion depth detection signal. Then, the controller 400 performs a control of respective constitutional elements of the pressurized gas supplying and discharging device 300 and a control of the ultraviolet ray irradiation lamps 130 described in the above-mentioned respective embodiments based on the insertion depth detection signal.

(c) In a third modification of the insertion depth detection unit, a light emitting element and a light receiving element (not shown in the drawings) are arranged to face each other at a predetermined position in the sterilization chamber 110. Then, the insertion depth detection unit detects that a predetermined portion (for example, a fingertip of any one of five fingers) of a hand on which a glove (1 is mounted blocks a light from the light emitting element based on a signal transmitted from the light receiving element, and outputs an insertion depth detection signal which indicates that the hand on which the glove G is mounted is inserted into the sterilization chamber 110 by a predetermined depth. Then, the controller 400 performs a control of respective constitutional elements of pressurized gas supplying and discharging device 300 and a control of the ultraviolet ray irradiation lamps 130 described in the above-mentioned respective embodiments based on the insertion depth detection signal.

(d) It is possible to selectively combine the insertion depth detection unit (bare skin detection unit 210) described in the embodiment 1, the insertion depth detection unit (operator identifier detection unit 220) described in the embodiment. 2, the first modification of the insertion depth detection unit described in the above-mentioned (a), the second modification of the insertion depth detection unit described in the above-mentioned (b), and the third modification of the insertion depth detection unit described in the above-mentioned (c).

(3) In the above-mentioned respective embodiments, the description has been made by assuming that the glove G is a glove of a type having a short length which covers a range from the fingertips to the wrist of the operator W. However, the glove G is not limited to such a glove, and the glove G may be a glove of a type having a long length which can cover a range from the fingertips to a portion close to an elbow of an operator W. The glove G and an arm cover may be used in combination. When the glove G and the arm cover are used in combination, it is sufficient to use at least one of the operator identifier detection unit described in the embodiment 2 and the respective insertion depth detection units in (a) to (c) described in the above-mentioned (2).

(4) In the above-mentioned respective embodiments, a planar shape of the insertion opening 120 is a rectangular shape. However, the planar shape of she insertion opening 120 is not limited to a rectangular shape. The shape of the insertion opening 120 may be, for example, an oblong shape, an elliptical shape or the like.

Figure 13:
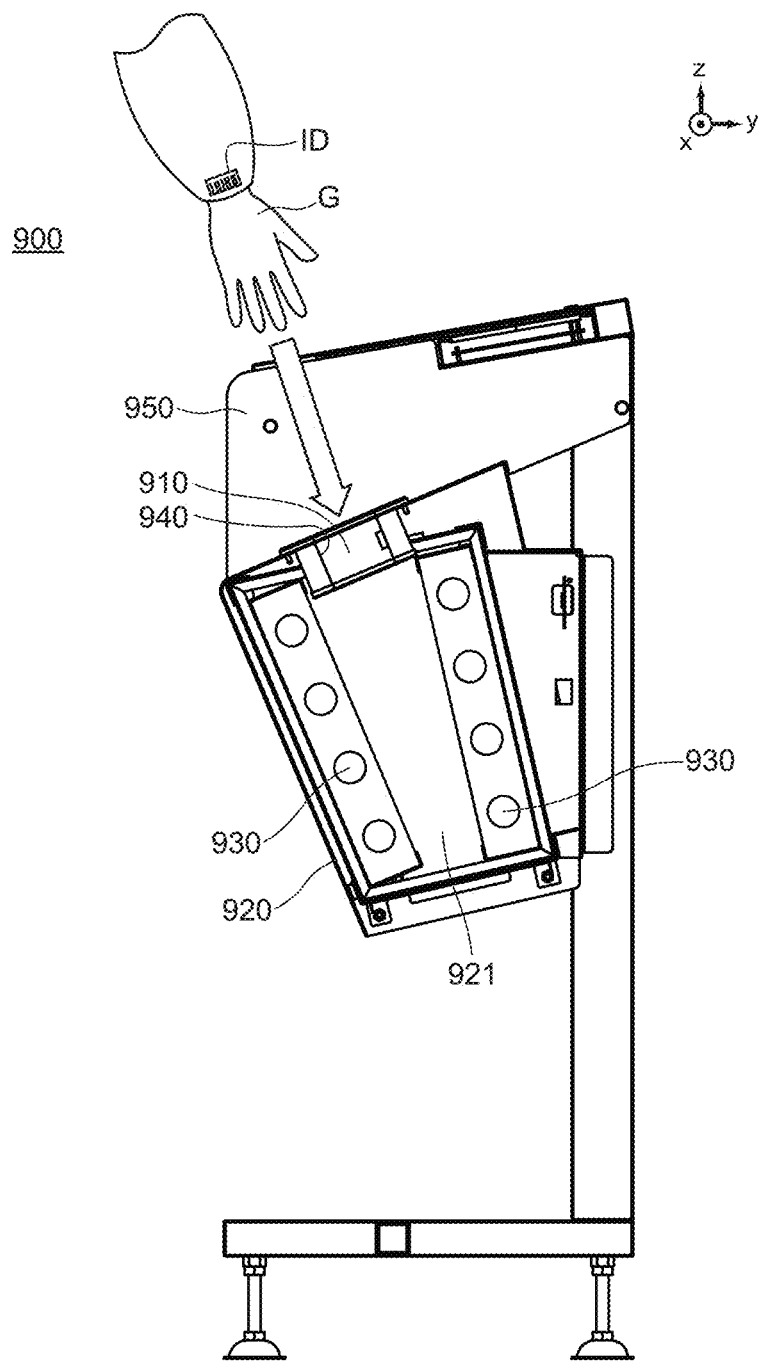
FIG. 13 is a view for describing an ultraviolet ray irradiation device 900 described in JP 2017-63900.

(5) The respective ultraviolet ray irradiation devices 10A to 10C shown in the above-mentioned embodiments are formed of an ultraviolet ray irradiation device of a type where, in inserting a hand on which a glove G is mounted into the sterilization chamber 110, the hand on which the glove G is mounted is inserted in an upward direction from below. However, like the ultraviolet ray irradiation device described in the above-mentioned "Description of the Related Art" (see FIG. 13), an ultraviolet ray irradiation device of a type where a hand on which a glove G is mounted is inserted in a downward direction from above may be also adopted. Although not shown in the drawings, an ultraviolet ray irradiation device of a type where a hand on which a glove G is mounted is inserted in an oblique upward direction, in an oblique downward direction or in a horizontal direction may be also adopted.

(6) In the above-mentioned embodiment 1 and embodiment 2, the case is exemplified where the ultraviolet ray blocking balloon 140 and the pressurized gas supplying and discharging opening 141 formed in the ultraviolet ray blocking balloon 140 are provided on a one to one basis. However, a plurality of (for example, two) pressurized gas supplying and discharging openings 141 may be formed in one ultraviolet ray blocking balloon 140.

(7) Antibacterial treatment is preferably applied, to a surface of the ultraviolet ray blocking balloon 140 described in the above-mentioned respective embodiments. Antibacterial treatment is also preferably applied to surfaces of the deflation assist belts 180.

What is claimed is:

1. An ultraviolet ray irradiation device which sterilizes a surface of a glove which is mounted on a hand of an operator and is made of an ultraviolet ray non-transmitting material by irradiating ultraviolet rays to the glove, the ultraviolet ray irradiation device comprising:
    a sterilization chamber housing formed of an ultraviolet ray blocking member configured to block the ultraviolet rays, the sterilization chamber housing having a sterilization chamber in the sterilization chamber housing, and having an insertion opening through which the hand on which the glove is mounted is insertable into the sterilization chamber;
    an ultraviolet ray irradiation unit disposed in the sterilization chamber housing and configured to irradiate the ultraviolet rays to the sterilization chamber;
    an ultraviolet ray blocking balloon having a sleeve shape, the ultraviolet ray blocking balloon being disposed along an edge portion of the insertion opening, the ultraviolet ray blocking balloon being made of an ultraviolet ray non-transmitting material;
    a pressurized gas supplying and discharging device configured to supply a gas under pressure to the ultraviolet ray blocking balloon and to discharge the gas supplied under pressure;
    an insertion depth detection unit configured to output an insertion depth detection signal when the hand on which the glove is mounted is brought into a state where the hand is inserted into the sterilization chamber by a predetermined depth is detected; and
    a controller configured to perform an ultraviolet ray irradiation control of the ultraviolet ray irradiation unit and a pressurized gas supplying and discharging control of the pressurized gas supplying and discharging device based on the insertion depth detection signal outputted from the insertion depth detection unit, wherein the ultraviolet ray blocking balloon forms an opening which allows an insertion and a removal of the hand on which the glove is mounted before the gas is supplied under pressure to the ultraviolet ray blocking balloon, the ultraviolet ray blocking balloon is inflated with a supply of the gas under pressure to the ultraviolet ray blocking balloon and surrounds a wrist portion of the glove in a state where the ultraviolet ray blocking balloon is brought into close contact with the wrist portion of the glove, and the ultraviolet ray blocking balloon is deflated with a discharge of the gas supplied under pressure and forms the opening which allows the insertion and the removal of the hand on which the glove is mounted.

2. The ultraviolet ray irradiation device according to claim 1, wherein the insertion depth detection unit is a bare skin detection unit configured to detect a bare skin of the operator, the bare skin detection unit is disposed at a position where a bare skin region right below the wrist portion of the glove can be detected when the hand on which the glove is mounted is brought into a state where the hand is inserted into the sterilization chamber by a predetermined depth, and is configured to output a base skin detection signal as the insertion depth detection signal when the bare skin region is detected.

3. The ultraviolet ray irradiation device according to claim 1, wherein the insertion depth detection unit is an operator identifier detection unit configured to detect an operator identifier attached to the wrist portion of the glove, the operator identifier detection unit is disposed at a position where the operator identifier can be detected when the hand on which the glove is mounted is brought into a state where the hand is inserted into the sterilization chamber by the predetermined depth, and is configured to output an operator identifier detection signal as the insertion depth detection signal when the operator identifier is detected.

4. The ultraviolet ray irradiation device according to claim 1, wherein the pressurized gas supplying and discharging device includes:
    a compressed gas generating unit for generating a compressed gas;
    a gas flow pipe disposed between the compressed gas generating unit and the ultraviolet ray blocking balloon and forming a flow path for the gas;
    a flow path switching valve disposed on an intermediate portion of the gas flow pipe; and
    a flow rate regulating valve mounted on the gas flow pipe disposed between the flow path switching valve and the ultraviolet ray blocking balloon, wherein
    the flow path switching valve has a function of switching a flow direction of a gas which flows through the gas flow pipe between a flow direction on a pressurized gas supply side where the gas is supplied under pressure to the ultraviolet ray blocking balloon and a flow direction on a pressurized gas discharge side where the gas supplied under pressure to the ultraviolet ray blocking balloon is discharged to an outside, and
    the flow rate regulating valve has a function of switching a flow rate of a gas which flows through the gas flow pipe between a flow rate on the pressurized gas supply side where the gas is supplied under pressure to the ultraviolet ray blocking balloon and a flow rate on the pressurized gas discharge side where the gas supplied under pressure to the ultraviolet ray blocking balloon is discharged to the outside, the flow rate on the pressurized gas supply side being set smaller than the flow rate on the pressurized gas discharge side.

5. The ultraviolet ray irradiation device according to claim 4, wherein the pressurized gas supplying and discharging device further includes a pressure regulating valve which has a function of regulating a pressure of a gas which the compressed gas generating unit generates to a predetermined pressure.

6. The ultraviolet ray irradiation device according to claim 4, wherein the controller is configured to perform a control of switching a flow direction of the gas to the flow direction on the pressurized gas supply side with respect to the flow path switching valve based on the insertion depth detection signal outputted from the insertion depth detection unit, to perform a control of switching a flow rate of the gas to the flow rate on the pressurized gas supply side with respect to the flow rate regulating valve, to perform a control of generating the gas with respect to the compressed gas generating unit, thereafter, to perform a control of starting irradiation of ultraviolet rays with respect to the ultraviolet ray irradiation unit, and when the ultraviolet ray irradiation unit performs the irradiation of the ultraviolet rays for a predetermined time, the controller is configured to perform a control of finishing the irradiation of the ultraviolet rays with respect to the ultraviolet ray irradiation unit, thereafter, to perform a control of stopping generation of a compressed gas with respect to the compressed gas generating unit, to perform a control of switching the flow direction of the gas to the flow direction on the pressurized gas discharge side with respect to the flow path switching valve, and to perform a control of switching a flow rate of the gas to the flow rate on the pressurized gas discharge side with respect to the flow rate regulating valve.

7. The ultraviolet ray irradiation device according to claim 1, wherein a plurality of deflation assist belts each having stretching and shrinking property for assisting deflation of the ultraviolet ray blocking balloon are mounted on a plurality of portions of an edge portion of the insertion opening in a circumferential direction in a spaced-apart manner from each other, and each of the deflation assist belt has a U-shaped folded shape, supports a peripheral surface of the ultraviolet ray blocking balloon on an inner surface side of a folded portion of the deflation assist belt having the U-shaped folded shape, and both end portions of the deflation assist belt having the U-shaped folded shape are mounted on the edge portion of the insertion opening.

8. The ultraviolet ray irradiation device according to claim 1, wherein the ultraviolet ray blocking balloon has an annular shape, and the ultraviolet ray blocking balloon having the annular shape is disposed so as to surround the edge portion of the insertion opening one turn along the edge portion.

9. The ultraviolet ray irradiation device according to claim 1, wherein the ultraviolet ray blocking balloon is formed of a plurality of ultraviolet ray blocking balloons, the plurality of ultraviolet ray blocking balloons are arranged in a longitudinal row so as to surround the edge portion of the insertion opening one turn along the edge portion.

10. The ultraviolet ray irradiation device according to claim 1, wherein a groove having a concave shape is formed on an edge portion of an insertion opening so as to extend along the edge portion one turn in a circumferential direction, and a surface of the ultraviolet ray blocking balloon on a side along the edge portion of the insertion opening is accommodated in the groove having a concave shape.

11. The ultraviolet ray irradiation device according to claim 1, wherein antibacterial treatment is applied to a surface of the ultraviolet ray blocking balloon.

12. An ultraviolet ray blocking unit which is mounted on an ultraviolet ray irradiation device which sterilizes a surface of a glove which is mounted on a hand of an operator and is made of an ultraviolet ray non-transmitting material by irradiating ultraviolet rays to the glove, the ultraviolet ray blocking unit configured to prevent an irradiation of the ultraviolet rays to an outside of the ultraviolet ray irradiation device when the glove of the operator is inserted into the ultraviolet ray irradiation device, wherein the ultraviolet ray irradiation device comprises:

a sterilization chamber housing formed of an ultraviolet ray blocking member configured to block the ultraviolet rays, the sterilization chamber housing having a sterilization chamber in the sterilization chamber housing, and having an insertion opening through which the hand on which the glove is mounted is insertable into the sterilization chamber;

an ultraviolet ray irradiation unit disposed in the sterilization chamber housing and configured to irradiate the ultraviolet rays to the sterilization chamber;

an ultraviolet ray blocking balloon having a sleeve shape, the ultraviolet ray blocking balloon being disposed along an edge portion of the insertion opening, the ultraviolet ray blocking balloon being made of an ultraviolet ray non-transmitting material;

a pressurized gas supplying and discharging device configured to supply a gas under pressure to the ultraviolet ray blocking balloon and to discharge the gas supplied under pressure;

an insertion depth detection unit configured to output an insertion depth detection signal when the hand on which the glove is mounted is brought into a state where the hand is inserted into the sterilization chamber by a predetermined depth is detected; and a controller configured to perform an ultraviolet ray irradiation control of the ultraviolet ray irradiation unit and a pressurized gas supplying and discharging control of the pressurized gas supplying and discharging device based on the insertion depth detection signal outputted from the insertion depth detection unit, wherein the ultraviolet ray blocking balloon forms an opening which allows an insertion and a removal of the hand on which the glove is mounted before the gas is supplied under pressure to the ultraviolet ray blocking balloon, the ultraviolet ray blocking balloon is inflated with a supply of the gas under pressure to the ultraviolet ray blocking balloon and surrounds a wrist portion of the glove in a state where the ultraviolet ray blocking balloon is brought into close contact with the wrist portion of the glove, and the ultraviolet ray blocking balloon is deflated with a discharge of the gas supplied under pressure and forms the opening which allows the insertion and the removal of the hand on which the glove is mounted, and the sterilization chamber housing includes a sterilization chamber housing member in which the insertion opening is formed, and which forms one surface of the sterilization chamber housing by being mounted on the sterilization chamber housing, and the ultraviolet ray blocking unit includes: the sterilization chamber housing member; and the ultraviolet ray blocking balloon disposed along the edge portion of the insertion opening formed in the sterilization chamber housing member, and is detachably mounted on the sterilization chamber housing.

\* \* \* \* \*